(12) United States Patent
Fahim et al.

(10) Patent No.: US 10,075,657 B2
(45) Date of Patent: Sep. 11, 2018

(54) EDGELESS LARGE AREA CAMERA SYSTEM

(71) Applicant: Fermi Research Alliance, LLC, Batavia, IL (US)

(72) Inventors: Farah Fahim, Glen Ellyn, IL (US); Grzegorz W. Deptuch, Forest Park, IL (US); Pawel Grybos, Rzaska (PL); Robert Szczygiel, Cracow (PL); Piotr Maj, Cracow (PL); Piotr Kmon, Niepolomice (PL); David Peter Siddons, Cutchogue, NY (US); Joseph Mead, Manorville, NY (US); Abdul Khader Rumaiz, Nesconset, NY (US); Robert Kent Bradford, Aurora, IL (US); John Thomas Weizeorick, III, Naperville, IL (US)

(73) Assignee: Fermi Research Alliance, LLC, Batavia, IL (US)

( * ) Notice: Subject to any disclaimer, the term of this patent is extended or adjusted under 35 U.S.C. 154(b) by 12 days.

(21) Appl. No.: 15/214,933

(22) Filed: Jul. 20, 2016

(65) Prior Publication Data
US 2017/0026598 A1 Jan. 26, 2017

Related U.S. Application Data

(60) Provisional application No. 62/195,053, filed on Jul. 21, 2015.

(51) Int. Cl.
| | | |
|---|---|---|
| *H01L 27/146* | (2006.01) | |
| *H04N 5/32* | (2006.01) | |
| *G01N 23/2055* | (2018.01) | |

(52) U.S. Cl.
CPC ............ *H04N 5/32* (2013.01); *G01N 23/2055* (2013.01)

(58) Field of Classification Search
CPC ......... H01L 2224/0508; H01L 21/8221; H01L 23/15; H01L 27/0688
See application file for complete search history.

(56) References Cited

U.S. PATENT DOCUMENTS

| | | |
|---|---|---|
| 8,913,121 B2 | 12/2014 | Gesley |
| 8,957,504 B2 | 2/2015 | Chao-Yuan et al. |
| 8,980,746 B2 | 3/2015 | Kolics |
| (Continued) | | |

OTHER PUBLICATIONS

"Design and Tests of the Vertically Integrated Photon Imaging Chip", IEEE Transactions on Nuclear Science, vol. 61, No. 1, Feb. 2014, pp. 663-674, to Deputch et al.*

(Continued)

*Primary Examiner* — Kenneth J Malkowski
(74) *Attorney, Agent, or Firm* — Kermit D. Lopez; Luis M. Ortiz; Ortiz & Lopez, PLLC

(57) ABSTRACT

A detecting apparatus includes a multi-tier 3D integrated ASIC comprising one or more analog tiers and one or more digital tiers, and a sensor bonded to the multi-tier 3D integrated ASIC. The detecting apparatus includes an electrical substrate and a group of FPGAs or custom data management ASICs. The detecting apparatus also includes a thermal management system, a power distribution system and one or more connectors to transfer data to a data acquisition system configured for radiation spectroscopy or imaging with zero suppressed or full frame readout.

14 Claims, 27 Drawing Sheets

(56) References Cited

U.S. PATENT DOCUMENTS

| | | |
|---|---|---|
| 9,000,599 B2 | 4/2015 | Raorane et al. |
| 9,026,969 B2 | 5/2015 | Jang et al. |
| 9,219,038 B2 | 12/2015 | Horng et al. |
| 9,305,864 B2 | 4/2016 | Horng et al. |
| 9,337,063 B2 | 5/2016 | Chen et al. |
| 9,337,114 B2 | 5/2016 | Han et al. |
| 9,343,369 B2 | 5/2016 | Du et al. |
| 2009/0251939 A1 | 10/2009 | Kojima |
| 2009/0290680 A1 | 11/2009 | Turner et al. |
| 2014/0284752 A1 | 9/2014 | Kalliopuska et al. |
| 2016/0097864 A1 | 4/2016 | Vora |

OTHER PUBLICATIONS

"Forced Convective Interlayer Cooling in Vertically Integrated Packages", Thermal and Thermomechanical Phenomena in Electronic Systems, 2008, pp. 1114-1125 to Michel et al.*

Three-dimensional integrated circuit, Wikipedia, the free encyclopedia, printed Jun. 14, 2016, 10 pages.

Von Trapp, F., The Future of Image Sensors is Chip Stacking, 3D InCites, Sep. 15, 2014, 5 pages.

Vasile, S. et al., ASIC Readout Circuit Architecture for Large Geiger Photodiode Arrays, Goddard Space Flight Center, Greenbelt, Maryland, NASA Tech Briefs, Sep. 2012, 1 page.

Sullivan, C. T., Compound Semiconductor III-V Photonics, Sandia National Laboratories, 2 pages Hybrid Pixel Detectors, Advanced Photon Source, https://www1.aps.anl.gov/detectors/detector-development/hybrid-pixel-detectors, printed Jun. 14, 2016, 2 pages.

Yarema, R. et al, Vertically integrated circuit development at Fermilab for detectors, Topical Workshop on Electronics for Particle Physics (2012) Sep. 17-21, Oxford, U.K., 12 pages.

Flueckiger, J. et al., Addressing the Challenges of Photonic IC Design Via an Integrated Electronic/Photonic Design Automation Environment, Cadence Design Systems, https://www.cadence.com/content/darn/cadence-www/global/en_US/documents/tools/custom-ic-analog-rf-design/photonic-ic-design-wp.pdf, 6 pages.

Through-silicon via—Wikipedia, the free encyclopedia, printed Jun. 14, 2016, 3 pages.

* cited by examiner

EDGELESS LARGE AREA CAMERA SYSTEM

CROSS-REFERENCE TO PROVISIONAL APPLICATION

This patent application claims priority under 35 U.S.C. 119(e) to U.S. Provisional Patent Application Ser. No. 62/195,053 entitled "VERTICALLY INTEGRATED PHOTON IMAGING CHIP DETECTOR FOR X-RAY SPECTROSCOPY," which was filed on Jul. 21, 2015, the disclosure of which is incorporated herein by reference in its entirety.

TECHNICAL FIELD

Embodiments are generally related to a camera. Embodiments are also related to ceramic board or PCB with 3D (three dimensional) ASIC (Application Specific Integrated Circuit), wafer scale-large area sensor, FPGA (Field Programmable Gate Arrays), with cooling systems, data acquisition systems and other circuit components and devices. Embodiments further relate to an apparatus for an edgeless large area camera utilized in detection applications and methods of configuring such an apparatus. Embodiments further relate to a VIPIC (Vertically Integrated Photon Imaging Chip) camera.

BACKGROUND

Camera system's specifically optimized for X-ray Photon Correlation Spectroscopy (XPCS) involve imaging "speckle" patterns produced when a coherent beam of x-rays scatters off a disordered sample. The speckle pattern is essentially the superposition of many single-particle diffraction patterns produced by the atoms within the sample. As the atoms undergo motion, the speckle pattern changes, so XPCS can be used to study atomic dynamics at very short time and distance scales. Use of XPCS will continue to expand for applications associated with x-ray light sources in coming years, particularly as synchrotrons upgrade to increase coherence.

Speckle patterns produce an anomalously weak signal With average pixel occupancies <<1%, XPCS is not well suited to a traditional x-ray area detectors which read out every pixel on every exposure. Much of the data throughput would be spent processing empty pixels.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification claims, drawings, and abstract as a whole.

It is, therefore, one aspect of the disclosed embodiments to provide for a 3D Integrated camera system.

It is another aspect of the disclosed embodiments to provide for a large area camera with a large area sensor 3D bonded to an array of 3D integrated ASICs which is further connected to a PCB or ceramic board on one side and an array of FPGA's on the other side constituting a detector module. An array of detector modules can be then connected to a detector head which also includes a cooling system in close proximity to allow for thermal management of the system and a plurality of picozed modules to connect to a data acquisition system.

It is another aspect of the disclosed embodiments to provide for improved ASIC (Application Specific Integrates Circuit) functionality, components and devices.

It yet another aspect of the disclosed embodiments to provide an edgeless large area ASIC utilized in detection applications.

It still another aspect of the disclosed embodiments to provide a ceramic substrate upon which one or more ASIC layers of a multi-tier ASIC layer is electrically connected (e.g., bump bonded). Such a ceramic substrate can be, for example, a low thermal co-fired ceramic.

It is also an aspect of the disclosed embodiments to configure the aforementioned ceramic substrate (e.g., on the other side) with one or more FPGAs electrically connected (e.g., bump bonded) to constitute a detector module.

In yet another aspect of the disclosed embodiments, the detector head can behave as a data concentrator composed of several detector modules and other circuit components to transfer high speed data to a DAS (data acquisition system) capable of implementing real-time correlation algorithms.

It is another aspect of the disclosed embodiments to provide for an edgeless large are camera system.

The aforementioned aspects and other objectives and advantages can now be achieved as described herein. In an example embodiment, a three dimensional integrated edgeless pixel detector apparatus can be implemented, which includes a large area three tier three-dimensional detector having one sensor layer, and two ASIC layers comprising an analog tier and a digital tier configured for x-ray photon counting and time of arrival measurement and imaging. The camera system consisting of a detector head with a cooling system, connectors for data transfer to an external data acquisition system and several detector modules each containing several FPGAs and 3D integrated ASICs and sensor.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 23 depicts thermal resistors instead of VIPIC ASICs for thermal dissipation studies);

DETAILED DESCRIPTION

Figure 1:
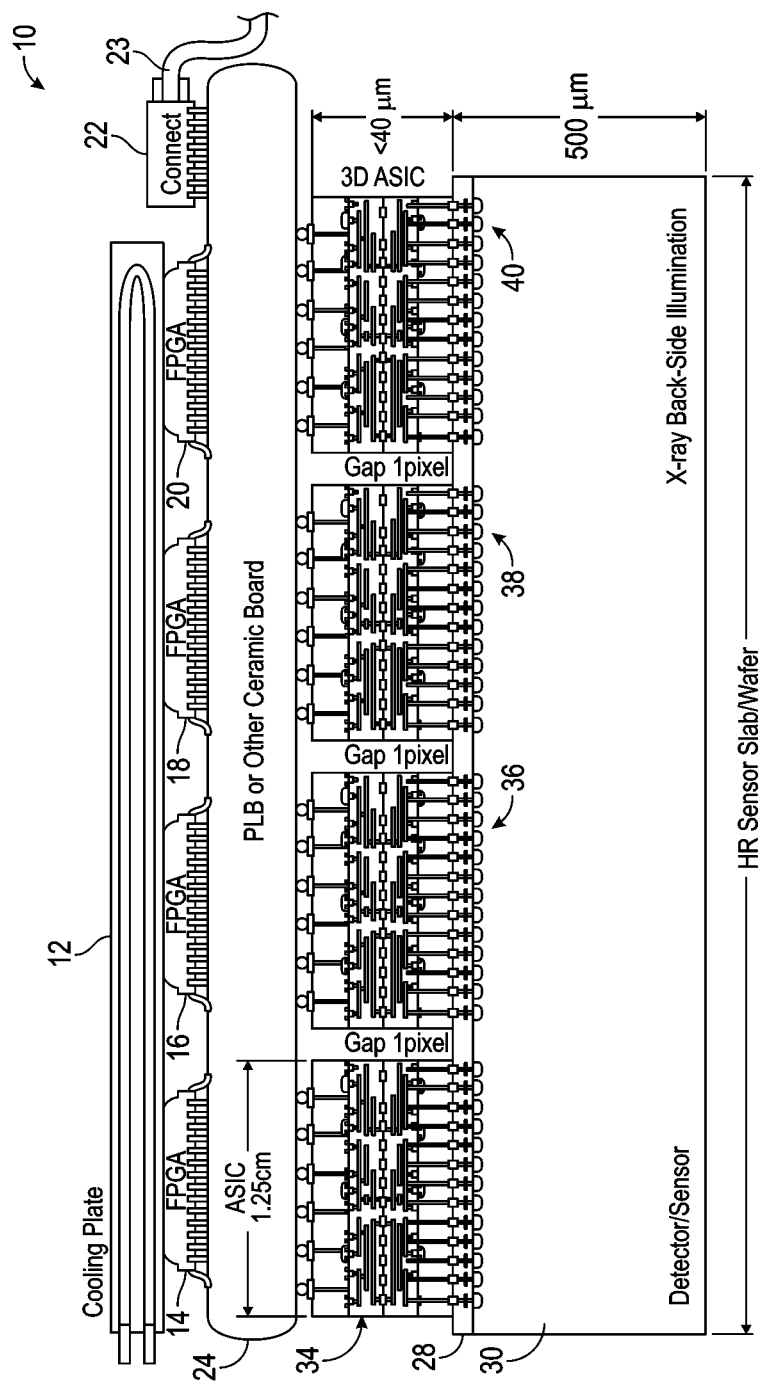
FIG. 1 illustrates a side cut-away view of a single module 3D integrated edge detector apparatus, in accordance with an example embodiment.

The particular values and configurations discussed in these non-limiting examples can be varied and are cited merely to illustrate one or more embodiments and are not intended to limit the scope thereof.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems.

Throughout the specification and claims, terms may have nuanced meanings suggested or implied in context beyond an explicitly stated meaning. Likewise, the phrase "in one embodiment" or "in one example embodiment" as used herein does not necessarily refer to the same embodiment and the phrase "in another embodiment" or "in another example embodiments" as used herein does not necessarily refer to a different embodiment. It is intended, for example, that claimed subject matter include combinations of example embodiments in whole or in part.

In general, terminology may be understood, at least in part, from usage in context. For example, terms, such as "and," "or," or "and/or" as used herein may include a variety of meanings that may depend, at least in part, upon the context in which such terms are used. Typically, "or" if used to associate a list, such as A, B, or C, is intended to mean A, B, and C, here used in the inclusive sense, as well as A, B, or C, here used in the exclusive sense. In addition, the terms "at least one" or "one or more" as used herein, depending at least in part upon context, may be used to describe any feature, structure, or characteristic in a singular sense or may be used to describe combinations of features, structures, or characteristics in a plural sense. Similarly, terms such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

As discussed previously, a detector specifically optimized for X-ray Photon Correlation Spectroscopy (XPCS) involves imaging "speckle" patterns produced when a coherent beam of x-rays scatters off a disordered sample. The speckle pattern is essentially the superposition of many single-particle diffraction patterns produced by the atoms within the sample. As the atoms undergo motion, the speckle pattern changes, so XPCS can be used to study atomic dynamics at very short time and distance scales. Use of XPCS will continue to expand for applications associated with x-ray light sources in coming years, particularly as synchrotrons upgrade to increase coherence.

Speckle patterns can produce an anomalously weak signal. With average pixel occupancies <<1%, XPCS is not well suited to a traditional x-ray area detectors which read out every pixel on every exposure. Much of the data throughput would be spent processing empty pixels.

A technique-specific detector utilizing a Vertically Integrated Photon Imaging Chip (VIPIC) can provide several unique capabilities designed to address the challenges of XPCS and enable new science. These properties include sparsified readout, high time resolution, and real-time calculation of auto-correlation functions.

Regarding sparsified readout, the VIPIC detector will increase data throughput by only reading out those pixels receiving an x-ray hit during the exposure window. The basic raw data is a simple list of hit times and pixel locations. The detector dispenses with the standard notion of an exposure producing a new imaging regime optimized for low-signal techniques.

Regarding high-time resolution, the detector can specify the interaction time of an x-ray to better than, for example, 10 microseconds. Standard area detectors simply record the location of the interaction, and the temporal resolution is determined by the exposure time.

Regarding real-time calculation of auto-correlation functions, the final result of an XPCS measurement is an auto-correlation function. The VIPIC detector will include novel readout electronics capable of real-time calculation of the auto-correlation functions. A practical detector for this purpose demands a large pixel count in order to acquire sufficient events to give good statistics.

The disclosed example embodiments discussed and illustrated herein cover various aspects of a very new technology of 3D integration that allows for an enhanced functionality in a hybrid pixel detector (e.g., a low noise, sparsified readout with a time stamp providing less than 10 microseconds precision). 3D integration comprises a method in which two separate CMOS circuits are bonded together, mechanically and electrically, to provide greater functionality than would be possible in a single CMOS layer. VIPIC utilizes a two-layer ASIC which will be directly bonded to a pixilated silicon sensor, and the resulting sensor/ASIC hybrids will be bump-bonded to a ceramic readout board. The unique hybrid structure does not require traditional wire-bonds for readout of the ASICs, eliminating many of the coverage gaps associated with traditional hybrid pixel area detectors.

Note that a TSV (through-silicon via) is a vertical electrical connection (via) passing completely through a silicon wafer or die. TSVs can be utilized to create 3D packages and 3D integrated circuits, compared to alternatives such as package-on-package because the density of the vias is substantially higher, and because the length of the connections is shorter.

FIG. 1 illustrates a side cut-away view of a single module 3D integrated edge detector apparatus 10, in accordance with an example embodiment. The apparatus 10 depicted in FIG. 1 can function as a 3D integrated edgeless pixel detectors and generally includes a cooling plate 12 disposed adjacent to a group FPGA (Field-Programmable Gate Array) devices 14, 16, 18, 20 configured on an LTCC (Low Thermal Coefficient Ceramic) substrate 24 in association with a connector chip 22 which in turn is electrically connected to a lead wire 23 for connection to other electrical devices and components. A group of ASIC devices 34, 36, 38, 40 is located below the LTCC substrate 24 at positions corresponding approximately to the locations of the respective FPGA devices 14, 16, 18, 20. The ASIC devices 34, 36, 38, 40 can form an ASIC array, and the FPGA devices 14, 16, 18, 20 can form an FPGA array. The ASIC devices 34, 36, 38, 40 are located on an oxide layer 28 that in turn is located above an HR sensor slab/wafer 30. The ASIC devices 34, 36, 38, 40 can form part of a 3D ASIC device.

A large area 3-tier 3D detector with one sensor layer, such as the sensor layer 30, and two ASIC layers containing one analog and one digital tier can be configured for x-ray photon counting and time of arrival measurement and imaging.

Figure 13:
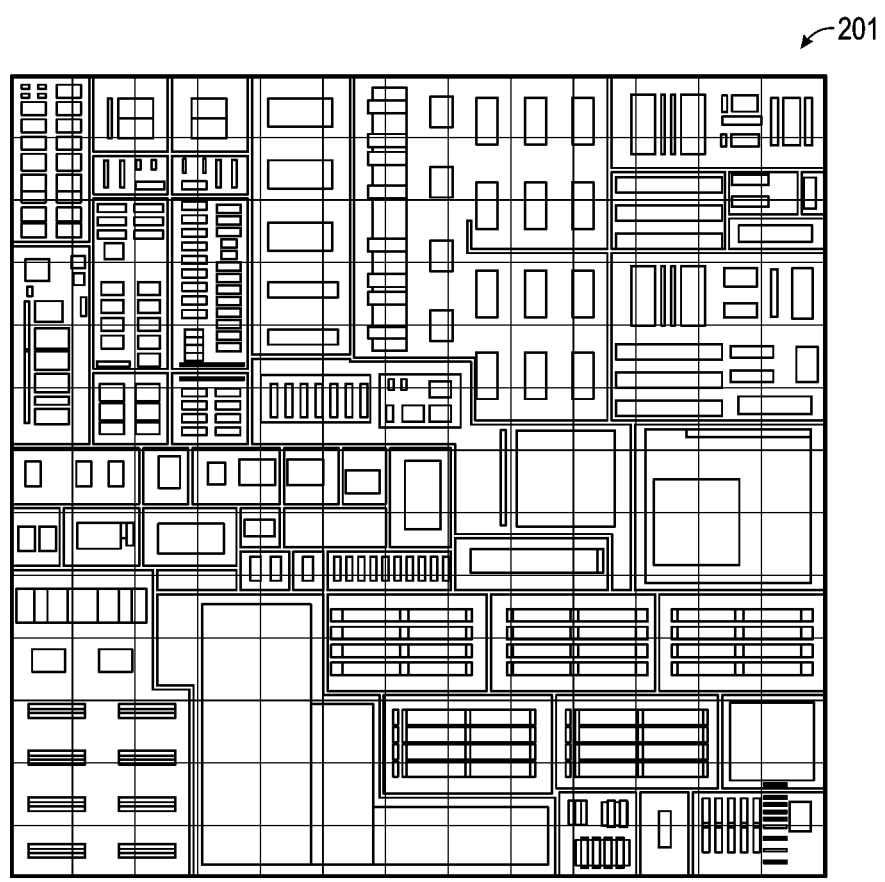
FIG. 13 illustrates a diagram of an analog pixel layout, in accordance with an example embodiment.

In some example embodiments, a full custom analog pixel such as the pixel 201 shown in FIG. 13 can be, for example, an analog pixel having a size of 65 μm×65 μm. Such an analog pixel can be connected to a sensor pixel of the same size on one side, and on the other side can offer approximately 40 connections to the virtual digital pixel.

The analog tier can be configured with no peripheral functional blocks. Hence, the active area extends to the edge of the detector. This arrangement can be achieved by utilizing a few flavors of almost identical analog pixels (e.g., with minimal variation in layout) to allow for peripheral biasing blocks to be placed within pixels.

In one embodiment, on the sensor tier, a large array of for example, 385×1157 array of for example, 65 μm×65 μm, will be connected to for example 12, 3D integrated ASICs, with sub-pixel or at most one pixel minimum gap between each ASIC. The 1 row and 5 columns of unconnected (to ASIC) pixels are connected to ground or left floating.

In another embodiment, on the sensor tier, a large array of for example, 384×1152 array of pixels will be connected to for example 12, 3D integrated ASICs, with a minimum gap of 65 μm between each ASIC. Such that 2 row and 10 columns of pixels located in between ASIC's are elongated to 1.5 times the size of the pixel to create a dead-zone less sensor system.

Figure 2:
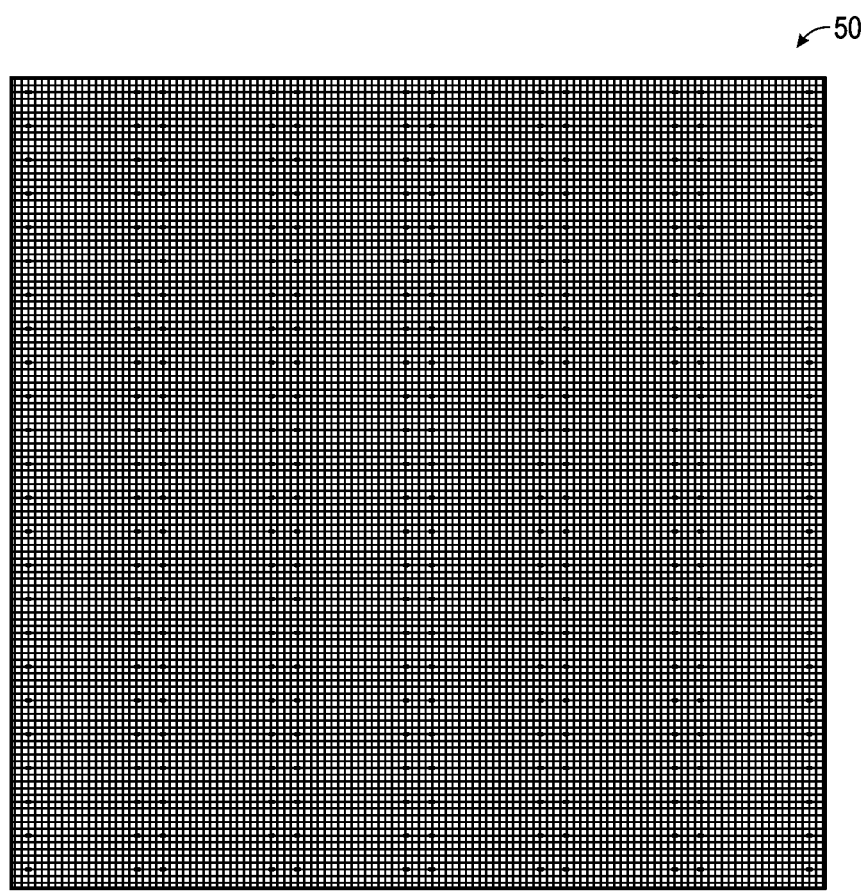
FIG. 2 illustrates a diagram depicting the layout of a VIPIC-L Analog Chip, in accordance with an example embodiment.

On the Analog ASIC tier, a 192×192 edgeless array has no peripheral functional blocks, for example. The pixels are arranged to create an entire 1.248 cm×1.248 cm ASIC as shown in FIG. 2. A small area within a 64×32 pixels is reserved for getting Analog I/O through the Digital tier from the PCB or other ceramic board. This I/O connectivity layout is repeated in a 3×6 array to provide connectivity for the entire ASIC.

On the Digital ASIC tier, a 32×32 edgeless array without any peripheral functional blocks, for example, constitutes a sub-chip. Such an example sub-chip can be an indivisible unit, which is further arranged in, for example, a 6×6 array to create an entire 1.248 cm×1.248 cm ASIC as shown in FIG. 3.

Figure 4:
FIG. 4 illustrates a diagram depicting the back of a VIPIC-L digital chip with names of the bump-bond I/O connections which need to be connected to the PCB or ceramic board in accordance with an example embodiment.

Each chip can include 720 bump-bond I/O connections shown in FIG. 4 on the back of the digital tier to the ceramic PCB or substrate such as, for example, the LTCC substrate 34 shown in FIG. 1. The entire analog tier power and biasing can be conveyed through the digital tier from the PCB or ceramic substrate 24.

FIG. 2 illustrates a diagram depicting the layout of a VIPIC-L Analog Chip 50, in accordance with an example embodiment.

Figure 3:
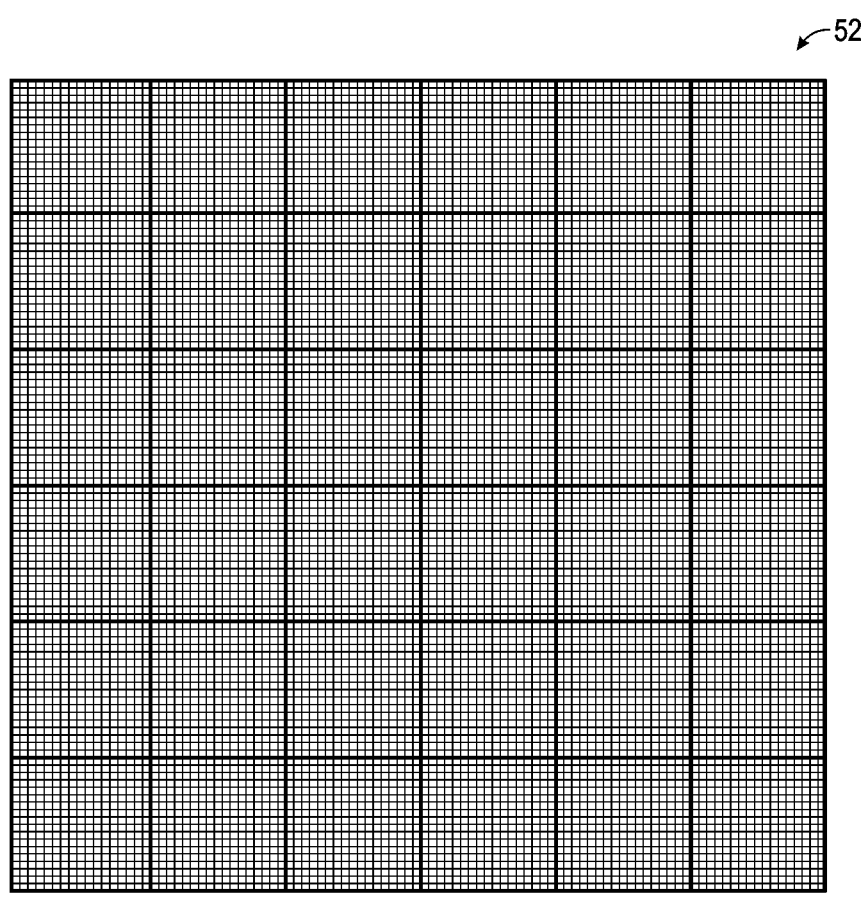
FIG. 3 illustrates a diagram depicting the layout of a VIPIC-L Digital Chip, in accordance with an example embodiment.

FIG. 3 illustrates a diagram depicting the layout of a VIPIC-L Digital Chip 52, in accordance with an example embodiment.

FIG. 4 illustrates a diagram depicting the back of a VIPIC-L digital chip 54 with example names of the bump-bond I/O connections which need to be connected to the PCB or ceramic board, in accordance with an example embodiment.

Figure 5:
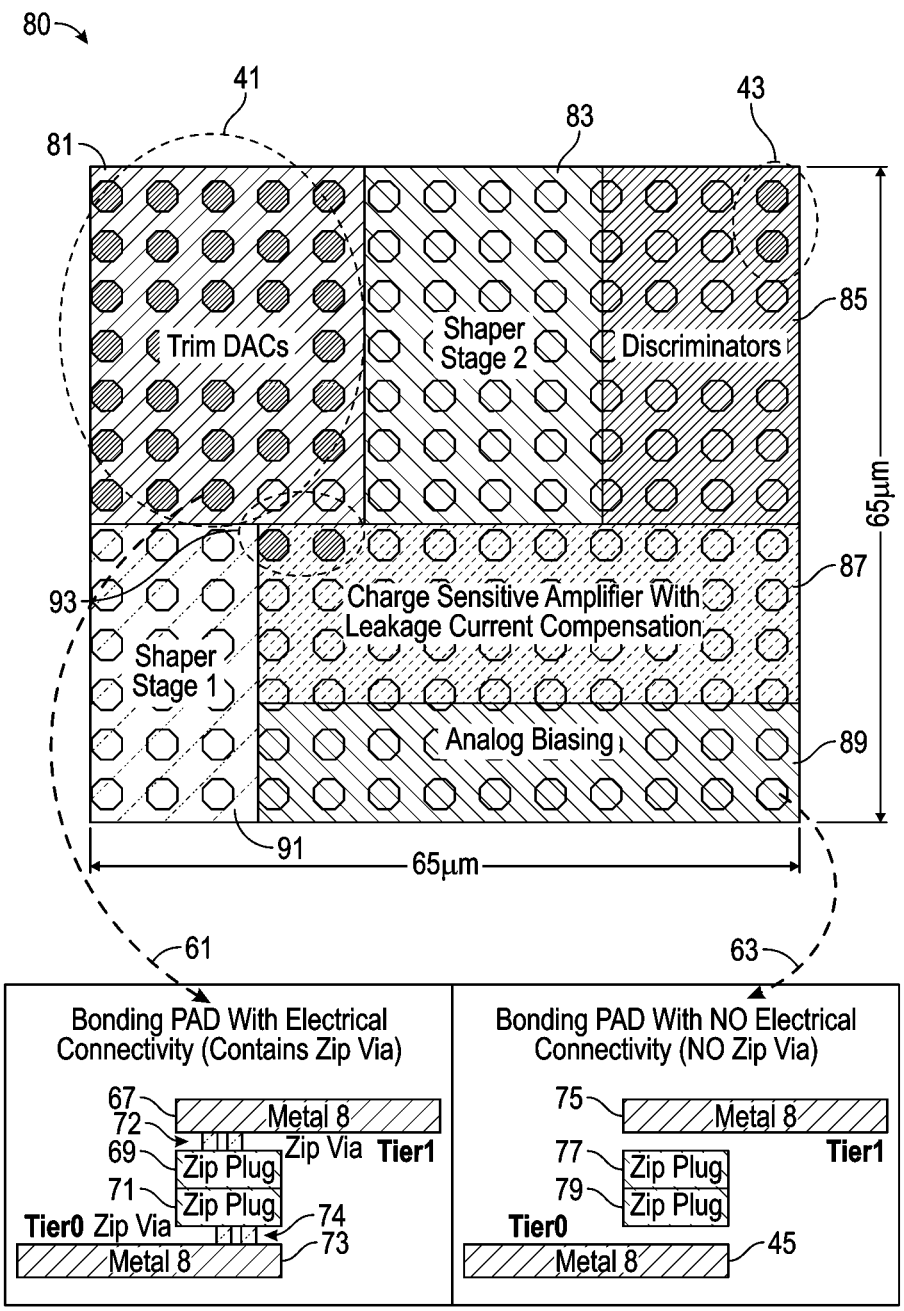
FIG. 5 illustrates an analog pixel bonding interface layout with locations of the various analog functional block layouts connecting to the analog pixel on one side and a part of the digital sub-chip on the other, in accordance with an example embodiment.

FIG. 5 illustrates the analog pixel bonding interface layout 80 with locations of the various analog functional block layouts connecting to the analog pixel on one side and a part of the digital sub-chip on the other. Approximately 25% of the bonding interface contains electrical connections between the analog and digital tier; these connections have a zip via 72 between the zip plug 69 and a metal trace 67 (i.e., metal 8). A zip via 74 is located between the zip plug 71 and a metal trace 73 (i.e., metal 8). The rest of the connections provide mechanical bonding and do not contain a zip via.

The layout 80 depicted in FIG. 5 includes six areas 81, 83, 85, 87, 89, and 91. Area 81 is an area dedicated to trimming digital-to-analog converters offering configuration setup bits with respect to the analog section for digital-to-analog converters for offset corrections and gain controls. This section is shown in FIG. 5 as offering electrical connectivity through dark solid hexagons. Sections not offering electrical connectivities are open hexagons. The dashed circle 41 shown in FIG. 5 refers to configuration setup bits to the analog section for DAC and gain control.

The section or area 83 is a "Shaper Stage 2" section and does not have any electrical connections (i.e., non-electrical connections). The area 85 of the layout shown in FIG. 3 is dedicated to discriminators and includes, for example, discriminator outputs to the digital tier as indicated by the dashed circle 43. Area 87, shown in FIG. 5, is dedicated to a charge sensitive amplifier with leakage current compensation. The area 89 is dedicated to analog biasing (e.g., 5 um pitch (13×13 array per pixel)), and the area 91 is dedicated to a "Shaper Stage 1" section. A small area 93 is dedicated to strobe signals and this area is a sub-section of area 87 (i.e., charge sensitive amplifier with leakage current compensation). Note that in the example depicted in FIG. 5, the layout is shown with dimensions of 65 um×65 um. It can be appreciated that these dimensions or parameters are examples only and should not be considered limiting features of the disclosed embodiments, similarly to the number of connections of the bonding interface carrying the electrical signals between the tiers.

The non-electrical connectivity arrangement or area 83 is shown in FIG. 5 to the right of the electrical connectivity configuration or area 81. This bonding PAD with NO electrical connectivity (NO Zip via) includes a metal layer 75 (Metal 8) above a Zip Plug 77 and a Zip Plug 79. A metal layer 45 (Metal 8) is also depicted in the non-electrical connectivity arrangement shown at the bottom left in FIG. 5.

Figure 6:
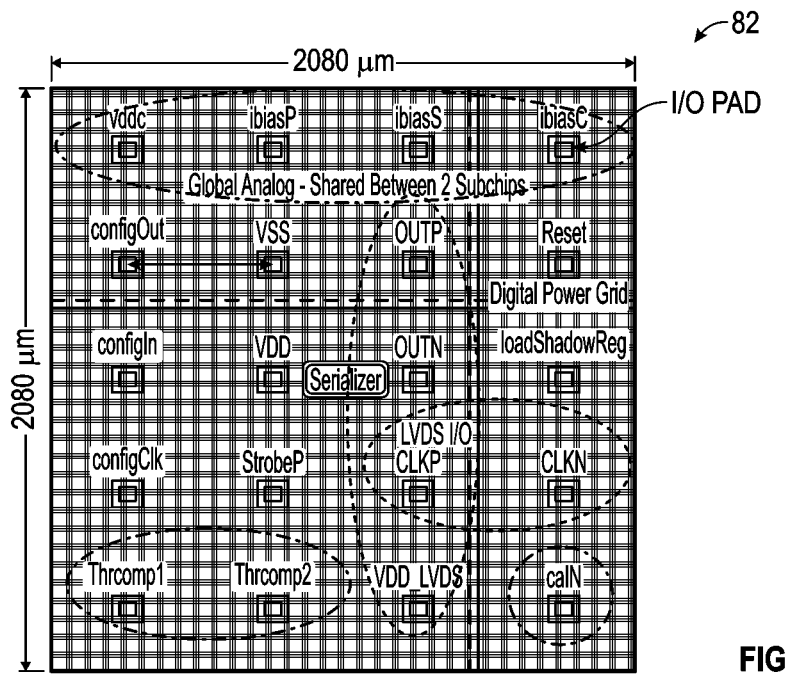
FIGS. 6-7 illustrate respective sub-chip layouts having the sub-chip digital functionality shown in FIG. 14, in accordance with an example embodiment.
Figure 7:
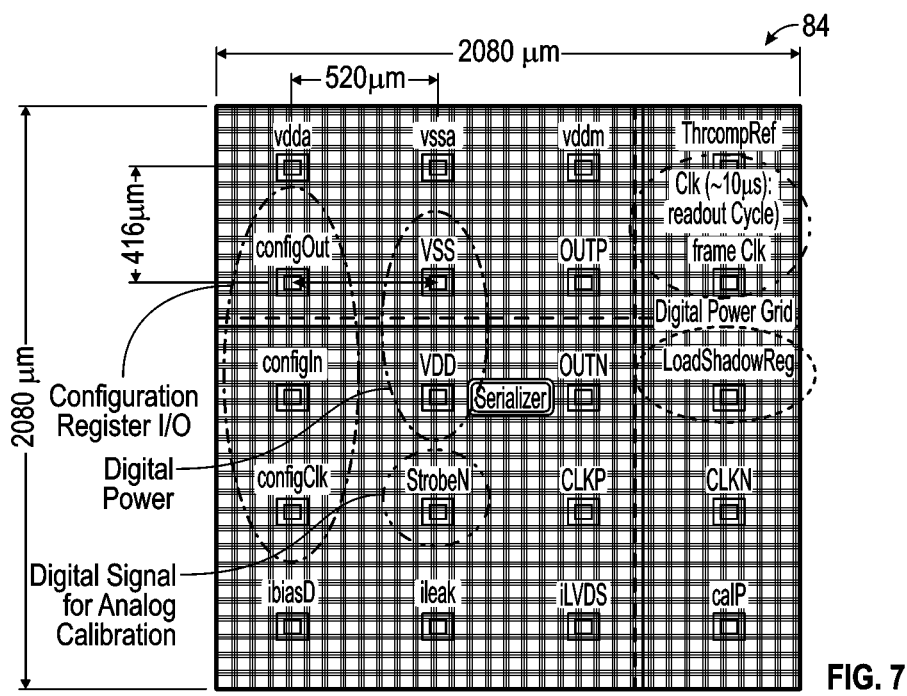
Figure 14:
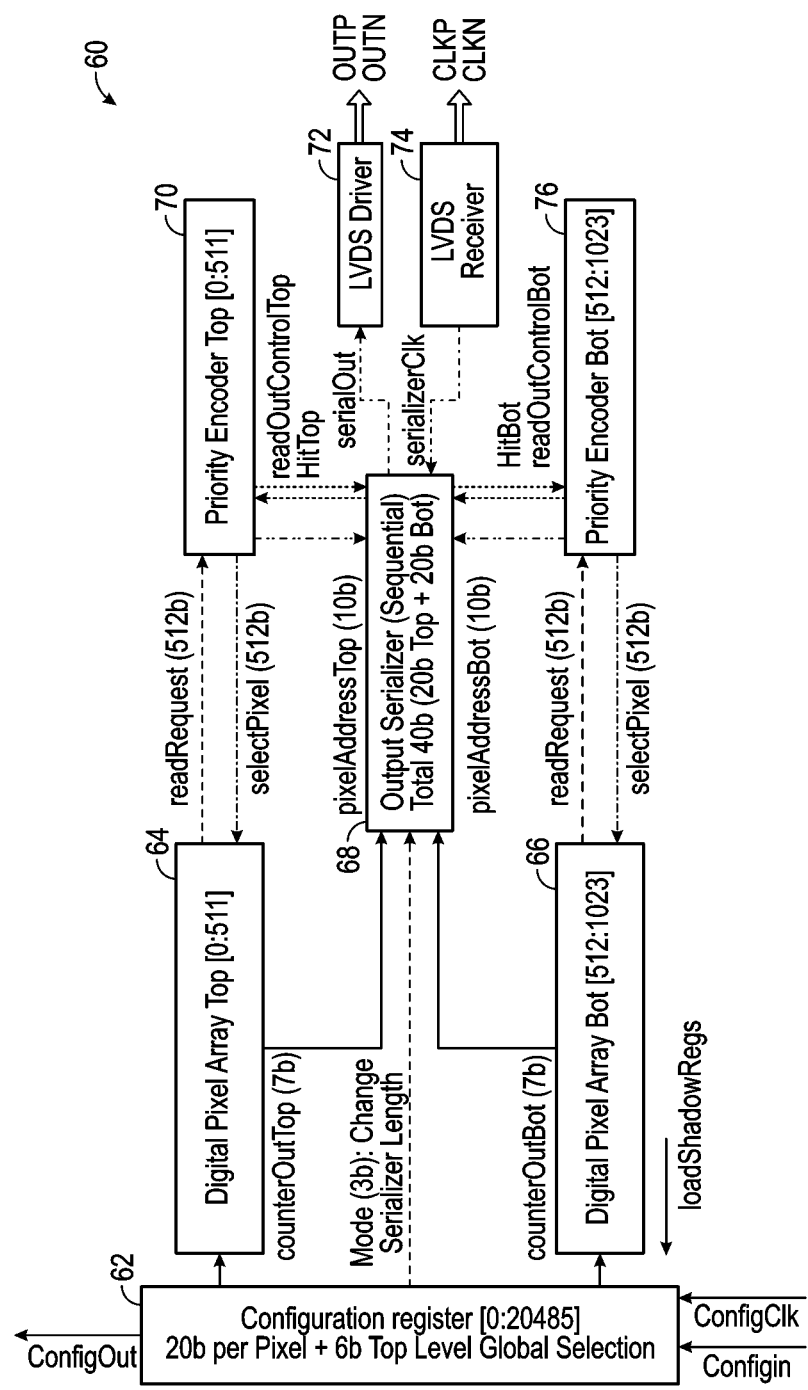
FIG. 14 illustrates a block diagram of a digital sub-chip, in accordance with an example embodiment.

FIGS. 6 and 7 illustrate sub-chip layouts 82 and 84 having the sub-chip digital functionality shown in FIG. 14, in accordance with an example embodiment. Each sub-chip can contain, for example, 20 bump-bond pads for external I/O's, they are created using back metal connected to Metal 1 in the ASIC via multiple B-TSVs (through-silicon vias) (preferably more than 100 per group). These bump-bond pads can, for example, 60 µm×60 µm in size, and can be placed with a horizontal and vertical pitch of, for example, 520 µm and 416 µm respectively. Routing of higher density bump-bond pads on the readout board would require very aggressive sizes and separation of traces. A total of, for example, 720 bump-bond pads can be utilized per VIPIC.

To minimize complexity, global signals can be shared between two sub-chips as shown in FIGS. 6 and 7. The 14 analog power and bias signals can be distributed on the top and bottom of the sub-chip, these need to be connected from Metal 1 to 9 on the digital tier, which is then electrically connected to Metal 9 of the Analog tier and subsequently distributed to the analog pixel. Shared signals can also include digital signals used for analog calibration, StrobeN and StrobeP, digital reset and frameClk. Configuration register clock and I/O and serializer differential I/O (e.g., see the output serializer 68 shown in FIG. 14) can be dedicated signals for a sub-chip.

The bump-bond pad sizes are approximately the same size as a pixel. The analog bump-bond pads, irrespective of their placement within a sub-chip, will partially overlap with inter-pixel electrical connectivity at fixed locations every, for example, 65 µm. Hence, these need to be custom designed to make sure that the inter-pixel connections are not shorted to global signals.

These bump-bond pads also create routing and placement restrictions in certain areas across the digital sub-chip. A power and ground grid for digital VDD and VSS can be created utilizing top two metal layers (e.g., vertical Metal 8 and horizontal Metal 7) approximately 10 µm wide at 65 µm pitch.

Figure 10:
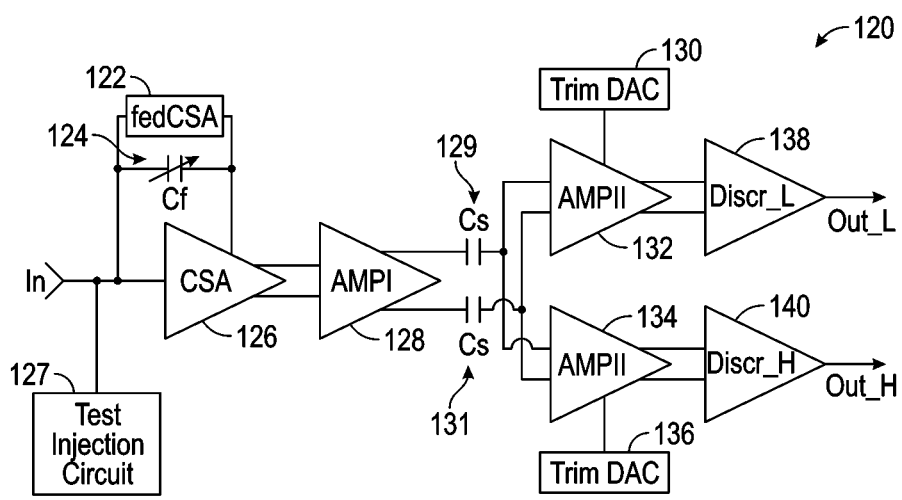
FIG. 10 illustrates a schematic diagram depicting an analog pixel circuit, which can be implemented in accordance with an example embodiment.

An embodiment of the analog pixel architecture (electrical circuit 120) is shown in FIG. 10, which contains a charge sensitive amplifier with leakage current compensation followed by a shaping amplifier, AC-coupled to the first stage of two comparator pre-amplifiers 132 and 134, and two additional comparators 138 and 140. Each of the comparator pre-amplifiers also receive inputs from trimming digital to analog converters (DAC) 130 and/or 136 for offset correction. The circuit 120 shown in FIG. 10 includes a test injection circuit 127 that is electrically connected to an input of the amplifier 126. A feedback CSA component 122 ("fedCSA") is also located in electrical series with a capacitor 124 and with the amplifier 126. The output from the amplifier 128 is input to amplifier 128, which in turn is connected in series with capacitors 129 and 131. The capacitors 129 and 131 connect electrically with amplifiers 132 and 134. The trim DAC components 130 and 136 are, respectively, connected to amplifiers 130 and 134. The output from amplifier 132 is connected to the input of amplifier 138 and the output from amplifier 134 is connected to the input of amplifier 140.

In an example embodiment, the window discriminator can contain two comparators with an upper and lower threshold to enable energy discrimination. Energy spectroscopy can be performed by increasing the number of comparators with additional thresholds within a pixel or using an in-pixel analog to digital converter (ADC).

Figure 11:
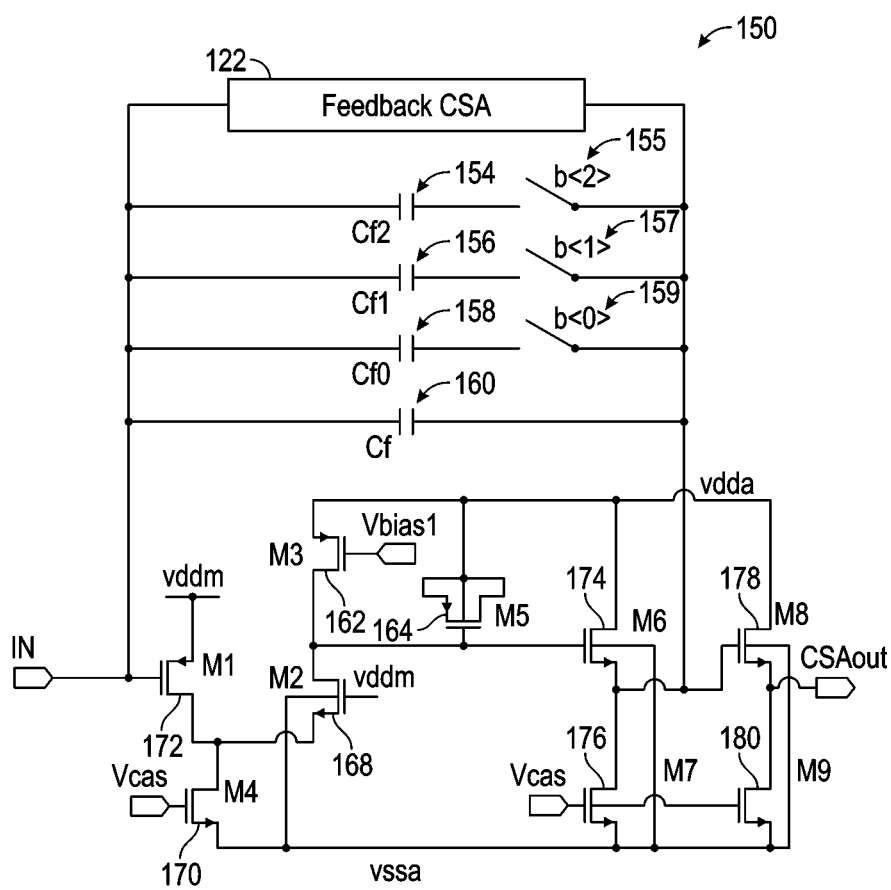
FIG. 11 illustrates a schematic diagram depicting a charge amplifier circuit, which can be implemented in accordance with an example embodiment.

A preamplifier circuit 150 is shown in FIG. 11; its feedback network contains a leakage current compensation circuit. It also contains additional capacitors in the feedback for gain trimming. The circuit 150 depicted in FIG. 11 includes the feedback CSA component 122 in parallel with capacitors 154, 156, 158, and 160. An electrical switching component 155 is associated with capacitor 154 and an electrical switching component 157 is associated with capacitor 156. An electrical switching component 159 is associated with capacitor 158. Additionally, a number of transistors, such as transistors 162, 164, 168, 170, 172, 174, 175, 178, and 180 are also included as a part of the circuit 150.

Figure 12:
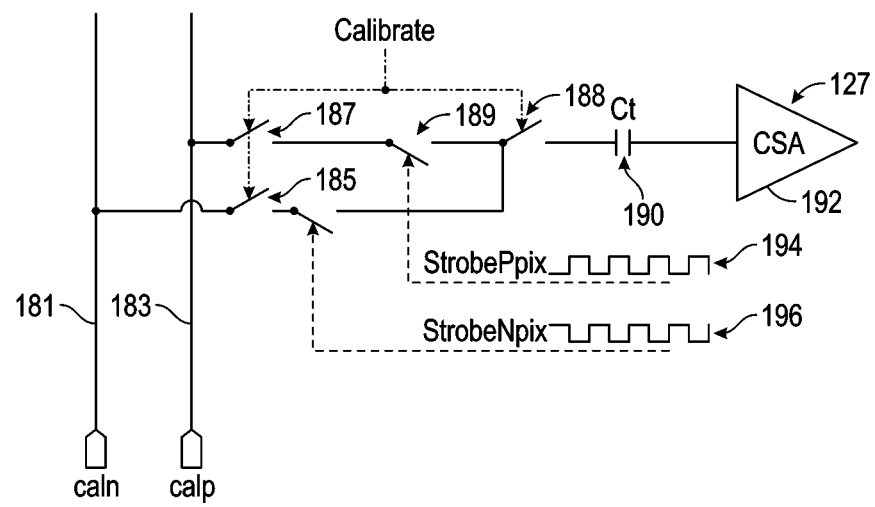
FIG. 12 illustrates a schematic diagram depicting a test injection circuit, which can be implemented in accordance with an example embodiment.

FIG. 12 illustrates a schematic diagram depicting in greater detail the test injection circuit 127 of FIG. 10, in accordance with an example embodiment. A test injection circuit such as circuit 127 is contained in each pixel and can be used for calibrating the pixel. The test injection circuit 127 can thus include two calibration input lines 181 and 183 electrically connected to a group of electrical switching components such as switches 185, 187, 188, and 189. The switch 188 connects to a capacitor 190 which in turn is provided as input to amplifier 192 (CSA). A strobePpix pulse

194 and a strobeNpix pulse 196 are also shown in the example embodiment depicted in FIG. 12.

The hit processor, accepts the output of the window discriminator from the analog tier and increments a, for example, a 7-bit gray-counter to register the number of photon hits in the pixel in a given time frame (frameClk). Since the pixel has two 7-bit counters for dead-time less operation, at any given time, one counter is in 'count mode' and the other is in 'read mode' if it had valid data in the previous frame or is 'idle'. At the rising edge of the frameClk, the counters which were in 'read mode' hut not yet read out will be reset, while those in 'count mode' with valid data will be swapped and placed in 'read mode'.

Counters, which were not used, can remain in the "count mode." This feature conserves power in low occupancy detector applications. The logic that checks if the counter is occupied and asynchronously resets it after readout, is extremely sensitive to glitches. Hence, a gray-code counter is preferable to a binary ripple counter to reduce the number of switching bits. Additionally, the choice of a gray-code counter reduces power consumption. Spill over protection logic eliminates the data recorded in the previous frame to be allocated to the wrong frame if the entire array was not fully read. Several user-defined functions can also be added such as utilizing only a single comparator instead of a window discriminator etc. The design is asynchronous, without the requirement of a high-speed clock tree distribution, as the data is generated by photon arrival. Full analog simulations were performed which clearly indicated that the design is sensitive to parasitics and a full custom layout, as disclosed herein, is required. 1024 hit processor full custom layout blocks can be strategically located across the sub-chip, close to the comparator outputs from the analog tier.

FIG. 14 illustrates a block diagram of a digital sub-chip 60, in accordance with an example embodiment. The digital sub-chip 60 shown in FIG. 14 includes a configuration register 62 the provides data to a first digital pixel array 64 (top) and a digital pixel array 66 (bottom). Output from arrays 64, 66 can be provided as input to an output serializer 68, which in turn communicates with a priority encoder composed of two encoder parts—a priority encoder 70 and a priority encoder 76. The output serializer 68 provides output that is fed as input to an LVDS driver 72. An LVDS receiver 74 outputs data that is fed as input to the output serializer 68. The priority encoder 76 (bottom) also communicates with the digital pixel array 66 (bottom) and the priority encoder 70 (top) communicates with the digital pixel array 64 (top). The priority encoder (e.g., see the priority encoder 70 top right in FIG. 14) and the priority encoder 76 (bottom right shown in FIG. 14) can be utilized for zero-suppression of data. This also increases the data throughput by only reading those pixels, which received photon hits during the time frame (exposure window) defined by the frameClk. The basic data is a simple list of counter value and pixel location. The priority encoder is a binary tree and also generates the address of the pixel. The priority encoder can be divided into the two parts (e.g., encoders 70 and 76 depicted in FIG. 14) each generating a 9-bit address for 512 pixels. This allows access of the two parts in an interleaved manner, providing enough time for the address bus to settle when a pixel is selected.

Figure 28:
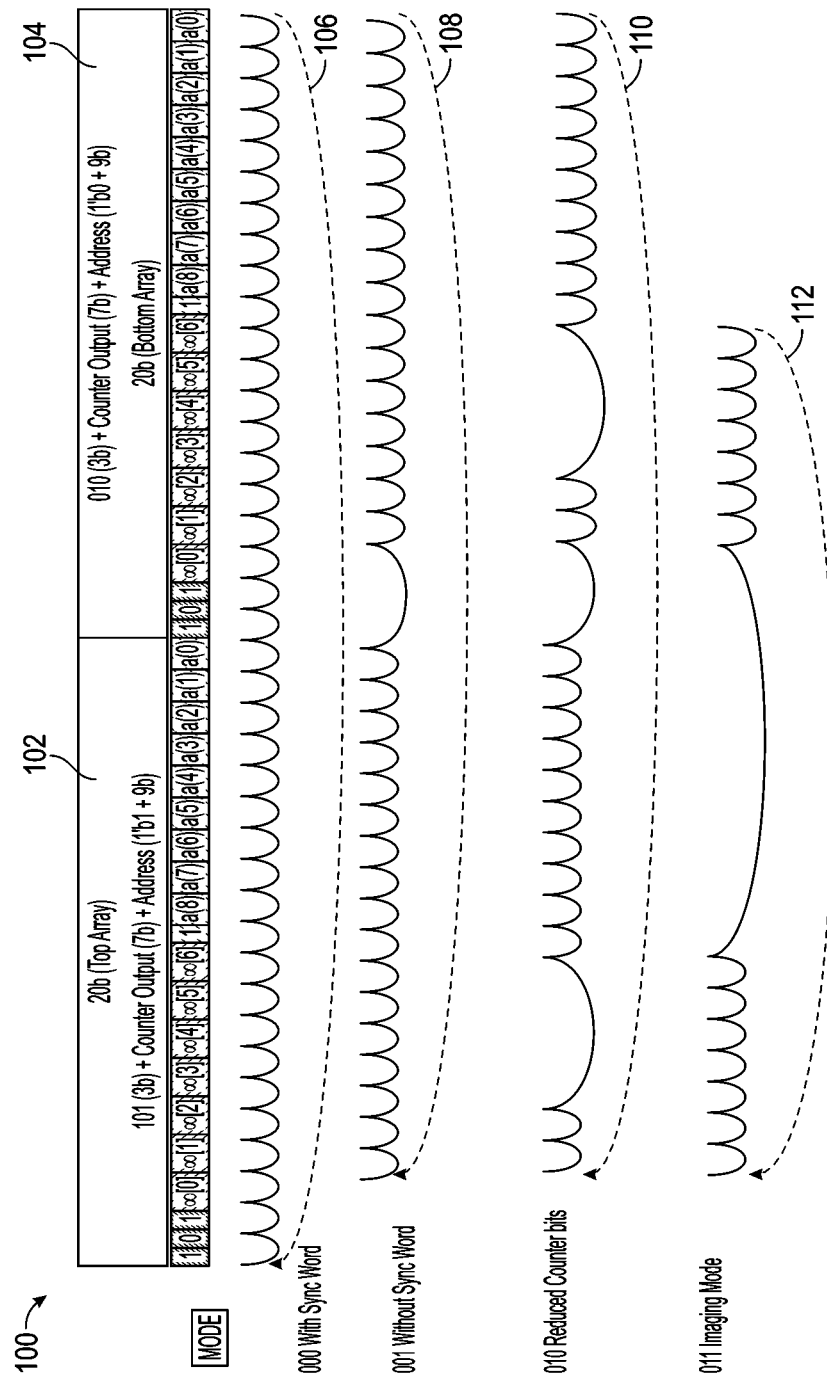
FIG. 28 illustrates examples of configurable readout modes, can change bit stream patterns, in accordance with an example embodiment.

FIG. 28 illustrates a schematic diagram depicting a readout from the output serializer 68 shown in 14 with respect to different modes of operation, in accordance with an example embodiment. The example different modes of operation depicted in FIG. 28 are modes 106, 108, 110, 112. Mode 106 involves "000 with sync word." Mode 108 involves "001 without sync word." Mode 110 involves "010 reduced counter bits" and mode 112 is a "011 imaging mode".

Regarding managing data transfer, photons arriving asynchronously at the detector generate a charge in the sensor, which can be processed by the analog pixel and subsequently events can be counted in the digital pixel within a certain time period. This time period can be determined externally by the user and defined within the ASIC as one period of the frameClk. The resolution of measure of photon time of arrival information can be determined by frameClk, which can typically range from a few hundred nanoseconds to a few tens of microseconds depending on the application. Typically, it is set at <10 µs. The change of frame caused by the rising edge of the frameClk creates a new priority list for pixel readout established by the priority encoder.

For certain applications, the frameClk rates need to be considerably faster than ~200 ns. However only 4 valid data packets at a data transfer rate of 50 ns/data packet can be read within this time frame. A really short exposure time, results in very few events. Hence a 7-bit counter will certainly not be fully occupied. Thus truncating the counter to, for example, 2-bits will be sufficient. Hence various readout modes are developed, to change the length of the data packet, which reduce the time for data transfer/packet.

The high-speed output serializerClk is independent of the slower ~1 µs frameClk, which are generally not aligned with each other. Although synchronizing the two clocks is possible, the application might require an independent setup of the frameClk and serializerClk. Furthermore, synchronization still does not guarantee correct alignment of the two signals at the pixel, because the clock tree for the frameClk is different from the path readoutControl (derived from the serializerClk) utilized through the priority encoder. The delays of these signals are position dependent and cannot be well controlled for a high-speed system. The power penalty from buffering and managing the clock tree of a slow clock with a high-speed clock is unnecessary, and practically unfeasible. However, it is important to ensure that data integrity is maintained during frame changes. A novel technique for ensuring that high priority data is not corrupted during frame changes can be implemented.

The full output data packet can include, for example, a 3-bit synchronization header, a 7-bit counter value and a 10 bit pixel address. This data can be serially transferred using high-speed differential outputs and an output serializerClk running at, for example, ~400 MHz.

Regarding readout modes, the data output of the ASIC can be either operated in a zero-suppressed or full-frame imaging format, which results in different data packet lengths. In the zero-suppressed format, the data packet needs to contain the 10-bit pixel address and between 2-7 bits of counter value, furthermore the 3-bit synchronization header is optional (but may be essential for debugging). In this case, for example a 20-bit data packet transfers a 3-bit start symbol, a 10-bit pixel address and a 7-bit counter value, requiring 50 ns to transfer a single data packet, or a 10-bit pixel address and 2-bit counter value, requires 30 ns. In the full imaging format, since every pixel is read out, only the 7-bit counter value is required, with 17.5 ns for readout per data packet, which achieves a 55 kfps for a 1 Mpixel detector. This may increase considerably if fewer counter bits are chosen.

FIG. 28 thus shows the main readout modes 106, 108, 110 and 112 discussed previously.

Maintaining data integrity at frame changes presents a challenge. During the current time frame, each pixel with valid data, sends a request signal for read out, to the priority encoder. The priority encoder (e.g., priority encoder (top) 70 and priority encode (bottom) 76) establishes the order in which the pixels are allowed to transfer data to the output serializer 68. The output serializer 68 allows a specific time window for the counter output to be transferred and the address to become available, such that it can be latched in time for off-chip data transfer (by the loadSerializer).

The rising edge of the frameClk, changes the frame. Counters in the 'readout mode' are reset, those in the 'count mode' are changed to 'readout mode' and those that are 'idle' do not change. Simultaneously, the priority encoder creates a new priority list by assigning the order in which multiple pixels are read out. The following signals are involved in data readout: frameClk, readoutControl, selectPixel (n), and load serializer.

The signal frameClk is a rising edge used to indicate change of frame (external slow clock). The signal readoutControl can be used to enable data transfer from a pixel to the serializer register, which is generated by the output serializer. This signal is interleaved between the two 512 pixel banks and is alternately broadcasted to the top pixel matrix and then to the bottom pixel matrix for pixel selection. The readoutControl pulse width is 2.5 ns corresponding to the serializerClk of 400 MHz. The time between the pulses of readoutControl is set by the readout mode depending on the number of output bits.

The rising edge of the frameClk, triggers the rising edge of readoutControl for both the top and bottom halves. This disables the last pixel being readout before the frame changes. The readoutControl is then held high up until at least one complete readout cycle is finished. The frameClk, distributed to the pixels is then delayed to the middle of the high state created on the readoutControl. This ensures the arrival of frameClk edge to any pixel in the matrix when readoutControl is high. Adjusting these signals in this manner leads to a minimal unavoidable dead-time in the readout of data. The following sequence with a time frame change is achieved on the output serial link: two unavoidably corrupted last data outputs, two known data patterns corresponding to frame change and then restarting readout with data from the top of the priority list in the new frame.

As discussed herein, in some examples, several readout modes can be implemented to allow the user to redefine a data packet and change the output data rate. It can therefore be appreciated that a novel technique and apparatus can thus be implemented, as disclosed herein, which can ensure that high priority data is not corrupted during frame changes.

Figure 8:
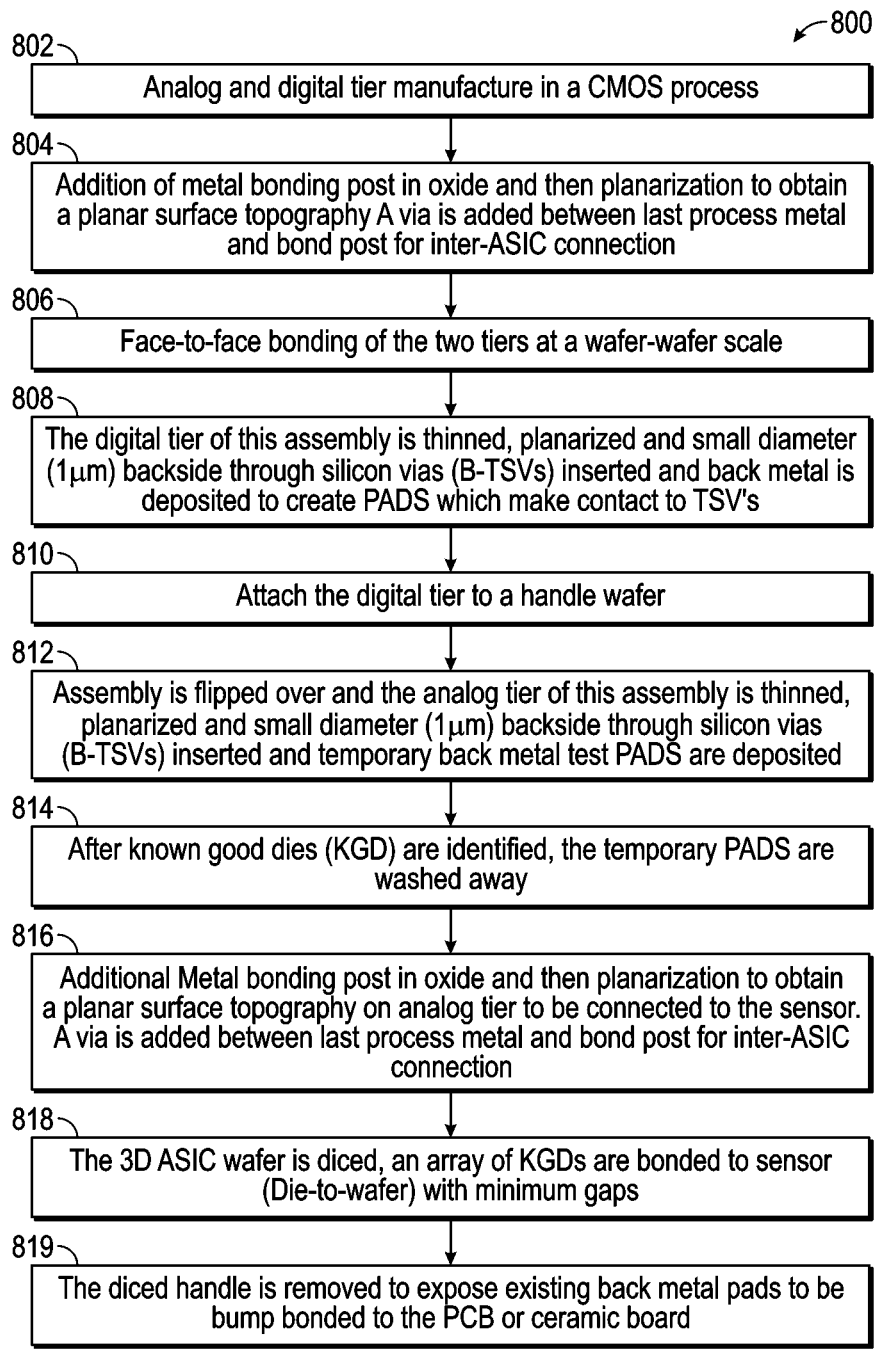
FIG. 8 illustrates a flow chart of operations depicting logical operational steps of a method for configuring an edgeless large area ASIC in accordance with an example embodiment.

FIG. 8 illustrates a flow chart of operations depicting logical operational steps of a method 800 for configuring an edgeless large area ASIC in accordance with an example embodiment. As shown at block 802, the analog and digital tiers discussed herein can be manufactured in a CMOS process. Then, as indicated at block 804, an operation can be implemented involving the addition of metal bonding post(s) in oxide followed by a planarization to obtain a metal surface topography with a via added between the last process metal and a bond post for inter-ASIC connection. Next, as illustrated at block 806, a face-to-face bonding step or operation can be implemented for face-to-face bonding of the two tiers at a wafer-wafer scale. The operation shown at block 806 involves face-to-face fusion bonding of the analog and digital ASIC tiers at the wafer-to-wafer level. Following processing of the face-to-face bonding operation depicted at block 806, a step or operation can be implemented as indicated at block 808, in which the digital tier of this assembly is thinned and planarized, and a small diameter (e.g., 1 um) backside is inserted through silicon vias (B-TSVs) and additionally a back metal is deposited to create PADS which make contact to TSVs. Next, as depicted at block 810, a step or operation can be implemented to attach the digital tier to a handle wafer. Thereafter, as indicated at block 812, a step or operation can be implemented to insert TSVs (through-silicon vias). The operation shown at block 812 involves flipping the assembly over and then thinning the analog tier of this assembly. The assembly is also planarized and the small diameter (1 um) backside is inserted through silicon vias (B-TSVs) and temporary back metal test PADS are deposited.

Following processing of the operation depicted at block 814, a step or operation can be provided to wash away the temporary PADS after a known good die (KGD) or known good dies (KGDs) are identified. Then, as shown at block 816, a step or operation can be implemented to add an additional bonding post in oxide and then planarized to obtain a planar surface topography on the analog tier to be connected to the sensor. A via can, be added between the last process metal and the bond post for inter-ASIC connection.

Figure 9A:
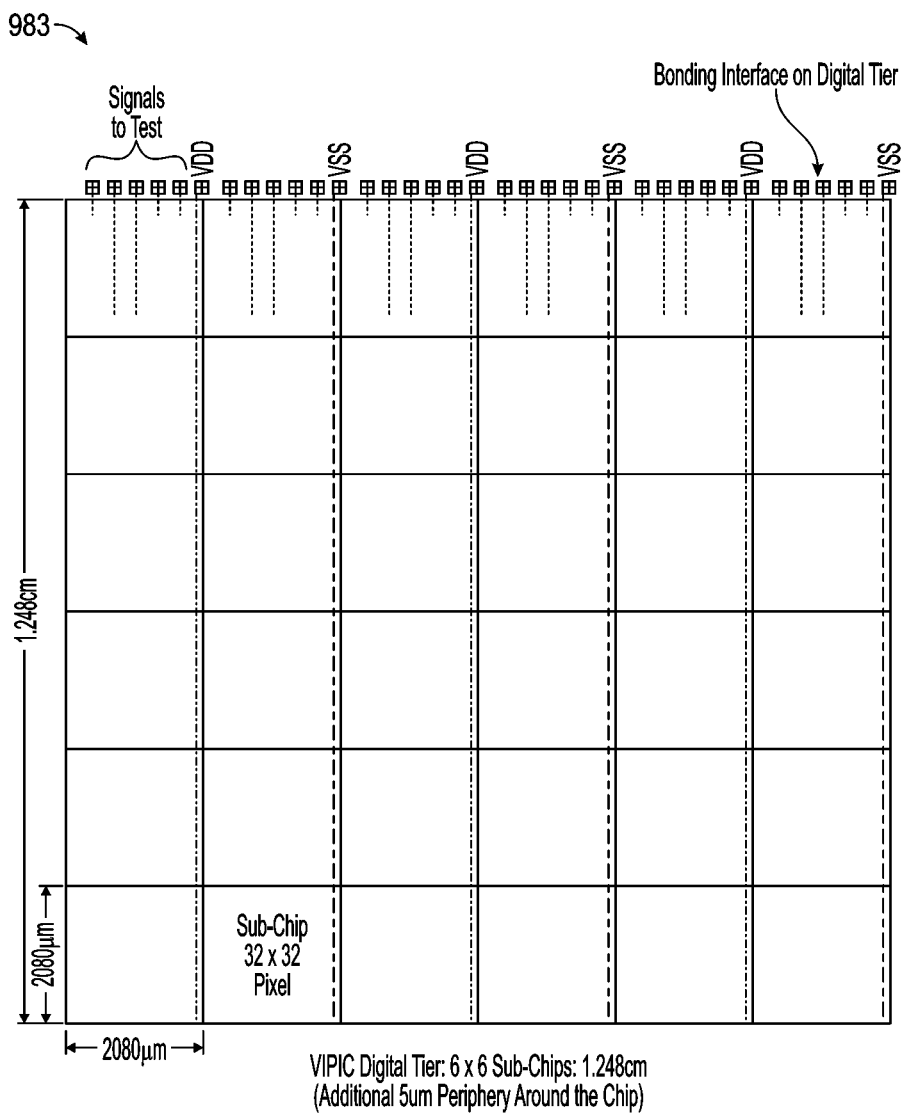
FIG. 9 illustrates layout diagrams of a VIPIC digital tier and a VIPIC analog tier having washable analog test PADS with connections in the analog tier, (Please note that these pads are not shown to scale, they fit in the 5 um boundary of a 1.25 cm×1.25 cm ASIC), in accordance with an example embodiment.
Figure 9B:
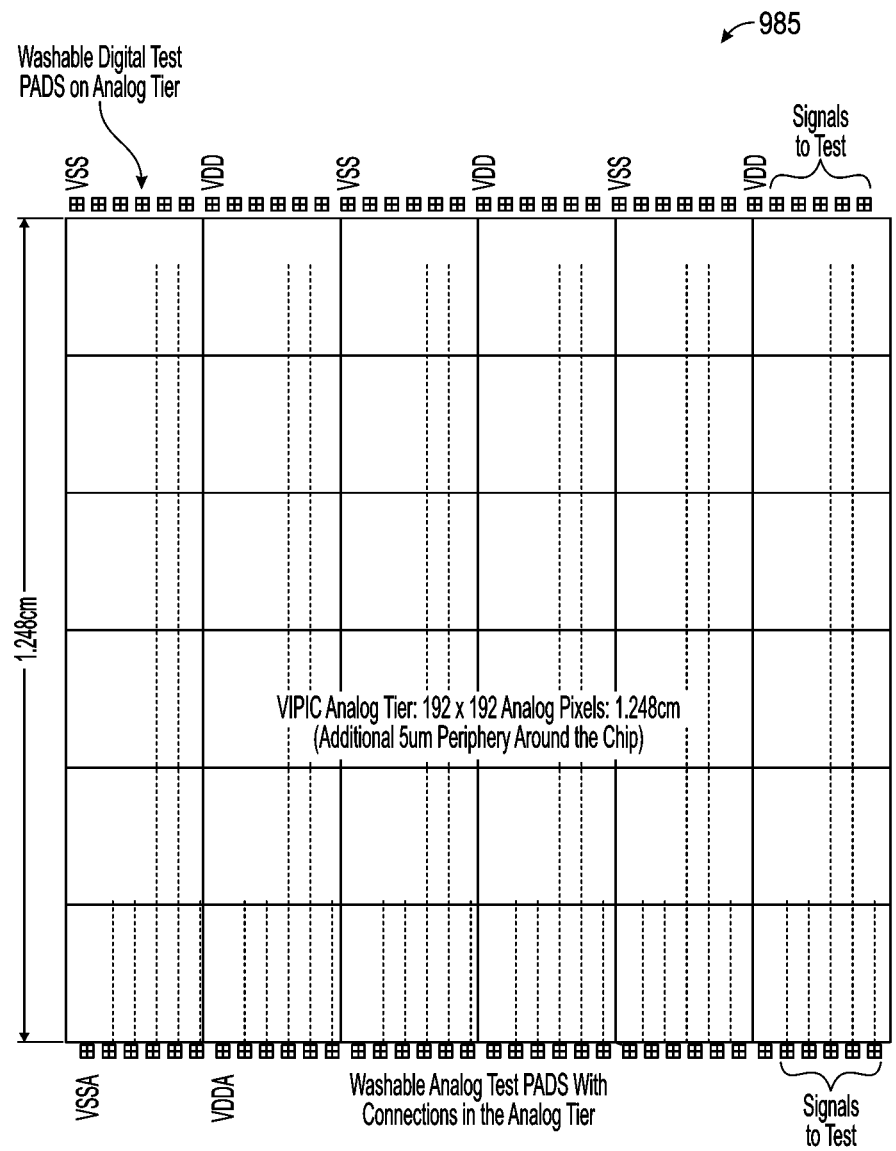

Temporary washable PADs as shown, for example, in FIGS. 9A and 9B can be added to test known good dies. Please note that the configuration depicted in FIGS. 9A and 9B is not to scale and the temporary washable pads are in the Sum periphery and the ASIC is approximately 1.25 cm×1.25 cm A map of known good dies is identified by testing the configuration register on the digital side and the analog biases on the analog side.

Thereafter, as shown at block 818, a step or operation can be implemented to dice the wafer and implement a die-to-wafer fusion bond array of KDG (known good die) to the sensor wafer. Then, as illustrated at block 819, a step or operation can be implemented to remove the handle wafer to expose the backside pads on the digital tier.

Figure 15:
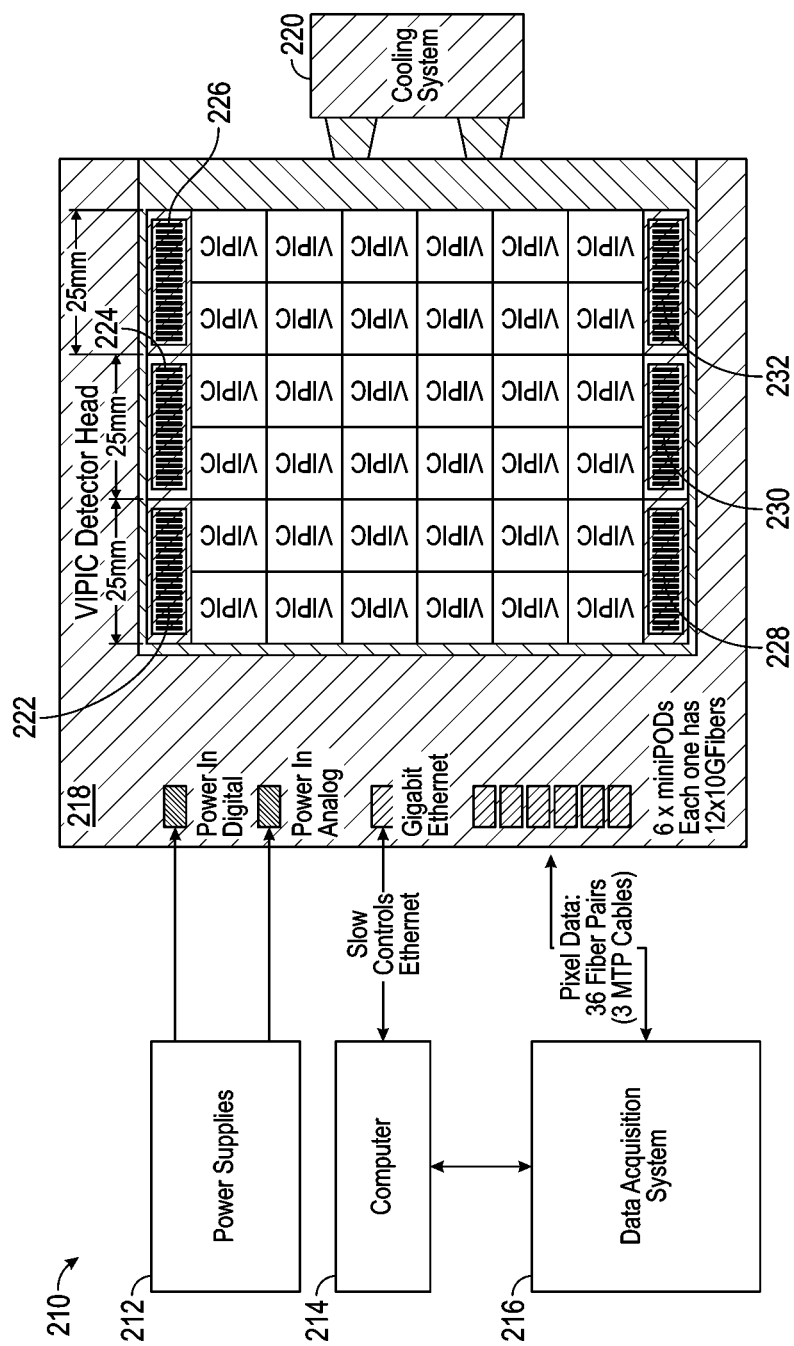
FIG. 15 illustrates a schematic diagram of a first part of the detector system in accordance with an example embodiment.

FIG. 15 illustrates a diagram of the entire VIPIC detector system 210, in accordance with an example embodiment. The VIPIC detector system 210 shown in FIG. 15 is composed of a detector head 218, a cooling system 220, a power supply 212, user interface computer 214 and a data acquisition system 216. The VIPIC detector head includes, for example a plurality of VIPIC detector modules 222, 224, 226, 228, 230 and 232.

Figure 16:
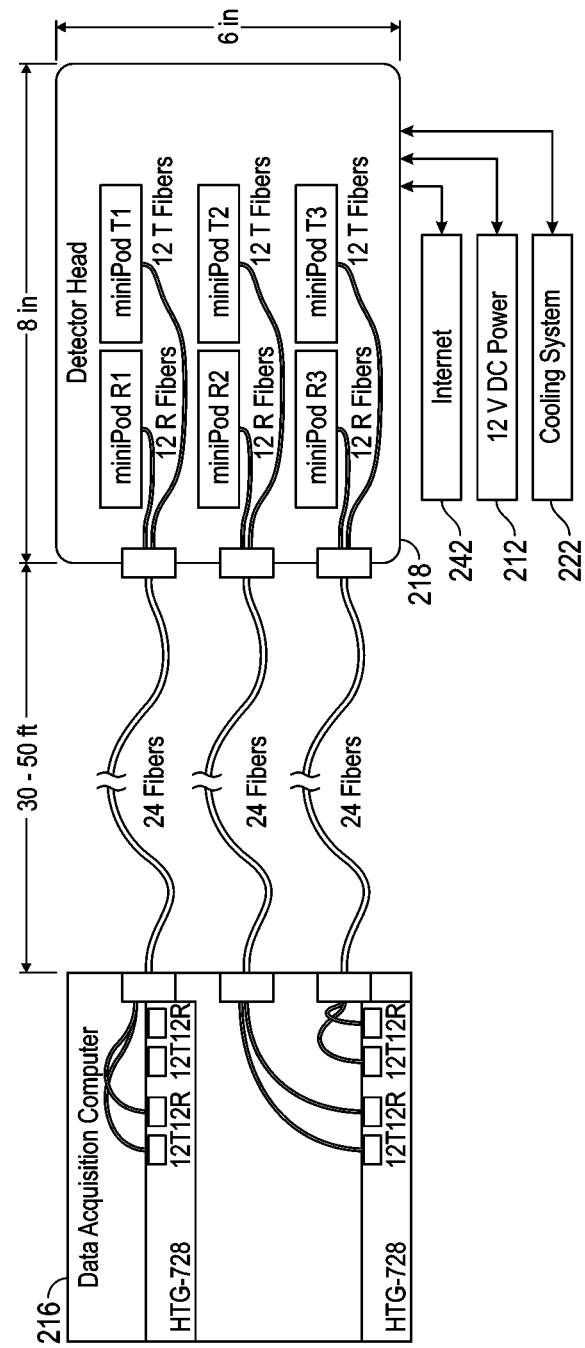
FIG. 16 illustrates a schematic diagram of a second part of the detector system, which can be implemented in accordance with another example embodiment.

FIG. 16 illustrates a schematic diagram of a second part of the detector system 210 shown in FIG. 15, in accordance with another example embodiment. The detector head 218 as shown in FIG. 16 is composed of a VIPIC motherboard, populated with three detector modules and a commercial PicoZED board. The detector head 218 communicates with a computer network such as the Internet 242 and with the cooling system 222. The data acquisition computer or system 216 is operably connected to the detector head 218 via one or more fibers (e.g., groups of 24 fibers). The detector head 218 is also powered by a 12 V DC power supply 212.

Figure 17:
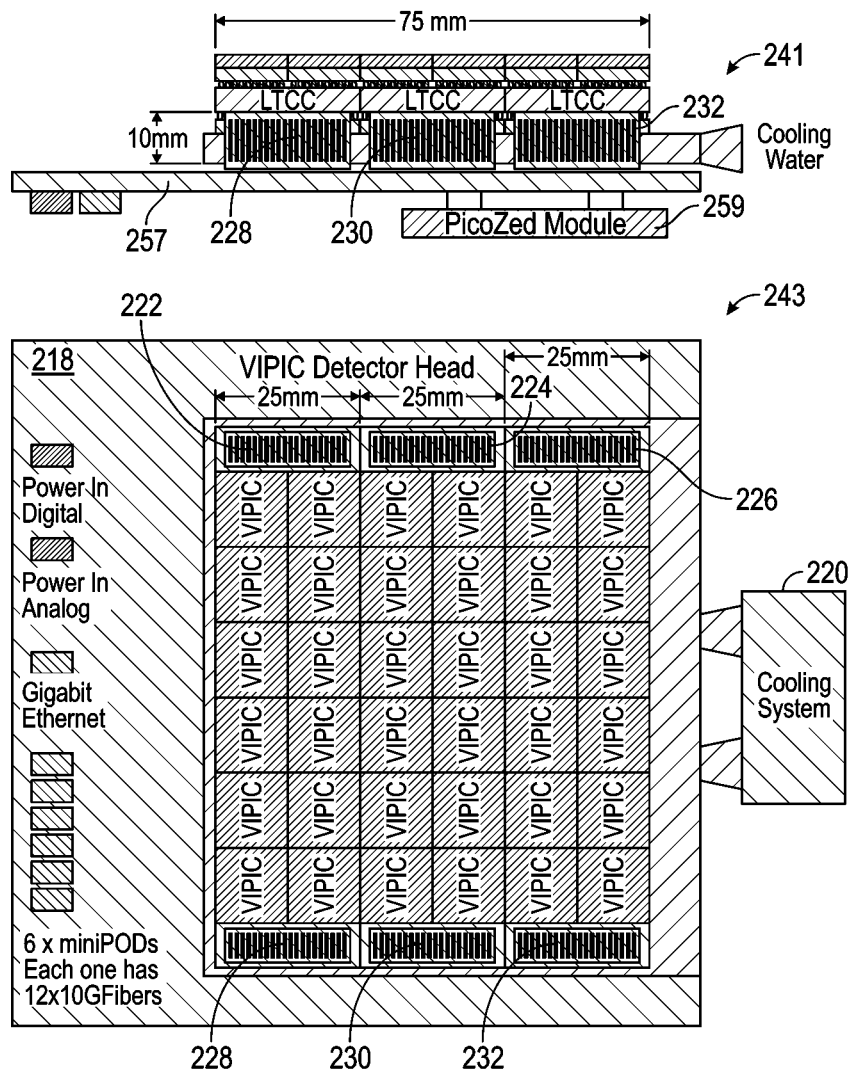
FIG. 17 illustrates a VIPIC motherboard with three detector modules installed and a PicoZed module, which can be implemented in accordance with an example embodiment.

FIG. 17 illustrates a side view 241 of a VIPIC motherboard with three detector modules installed and a PicoZed module, be implemented in accordance with an example embodiment. The VIPIC motherboard 257 as shown in FIG. 17 provides a number of features such as, for example, the ability to hold the PicoZED module 259 with Zynq FPGA running Linux. The configuration depicted in FIG. 17 can also hold the three example VIPIC detector modules 228, 230, 232. In addition, the VIPIC motherboard 257 depicted in FIG. 17 can provide system clocks to Artix chips and VIPIC ASICs, and also provide, for example, a 1 Gbit Ethernet Connection for slow controls, and a 10 Gbit Ethernet connection for faster communications. The arrangement shown in FIG. 17 can also provide for an SD card for PicoZED Linux and FPGA, and can also include 6 miniPODs, which have 12 fibers each and are used to communicate to the Artix FPGAs and through them transmit the VIPIC ASIC data. A side view 243 shown in FIG. 17 shows the detector head 218 details similar to what is shown in FIG. 15.

The system shown in FIG. 17 also allows the PicoZED to monitor and control two transmit and receive ports coming from two Artix chips and going to the miniPODs. Such a system can also include 22 voltage regulators to power PicoZED, Artix FPGAs. Additionally, the VIPIC ASICs can include a USB part for a Linux console and JTAG interfaces to Artix and PicoZED. Trigger inputs and outputs are also provided with respect to the FIG. 17 configuration.

Figure 19:
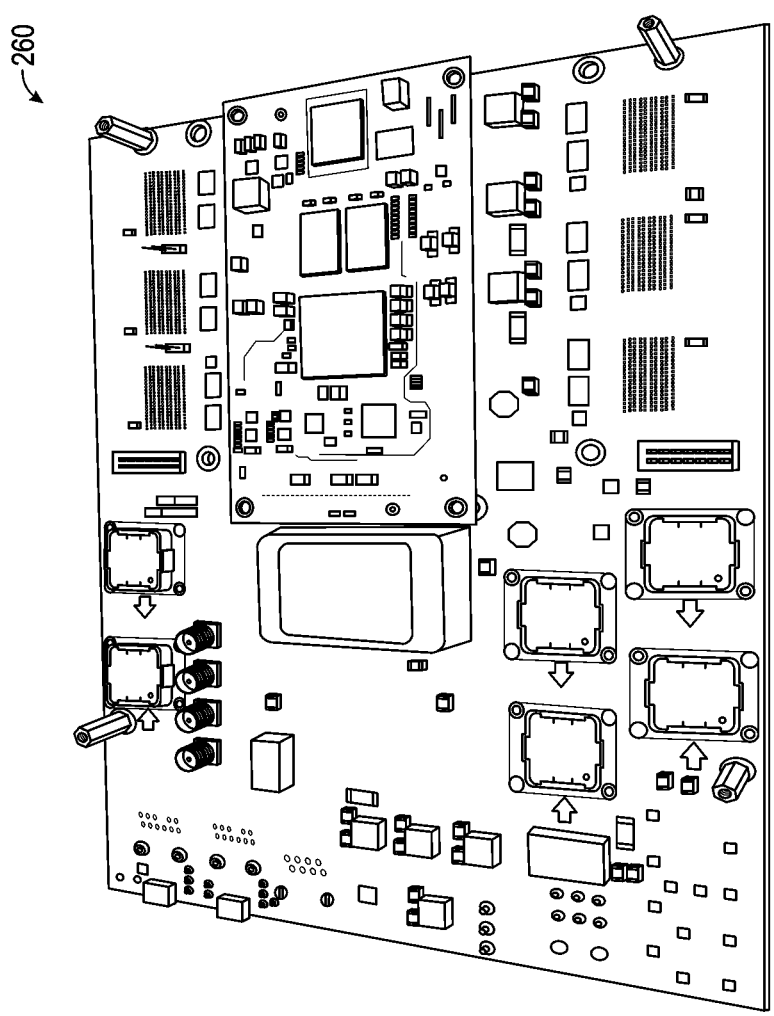
FIG. 19 illustrates an image of a VIPIC motherboard (view of the PicoZed Side), in accordance with an example embodiment.
Figure 20:
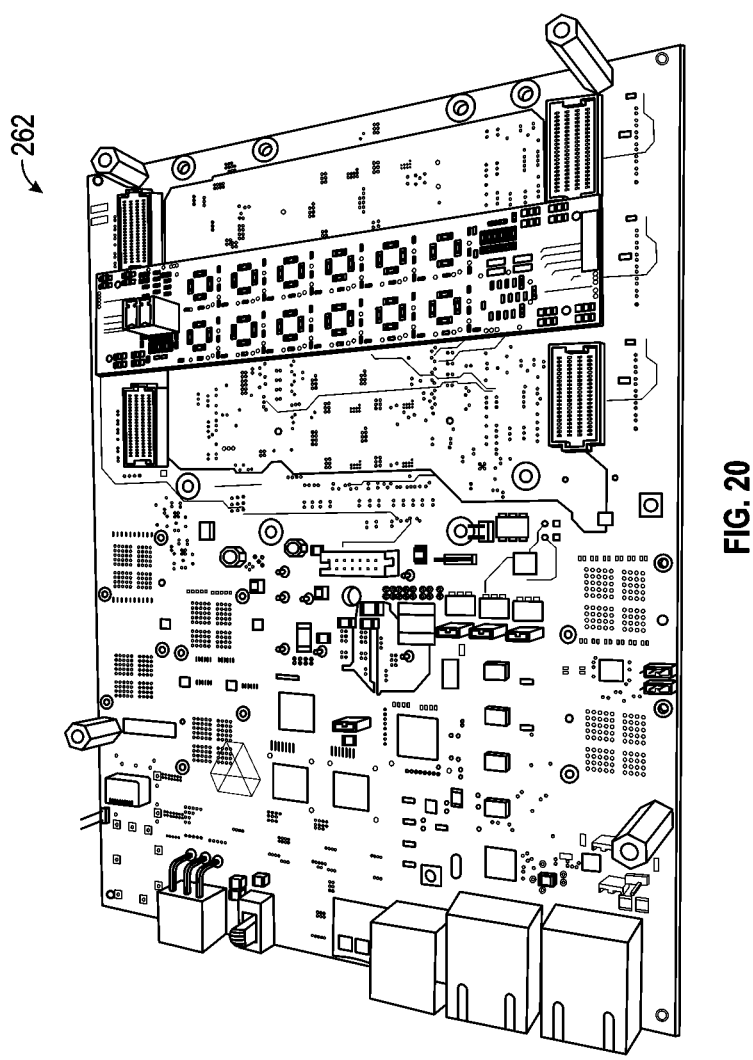
FIG. 20 illustrates an image of the VIPIC motherboard shown in FIG. 19 with a view from the detector module side, with one detector module plugged in, in accordance with an example embodiment.
Figure 21:
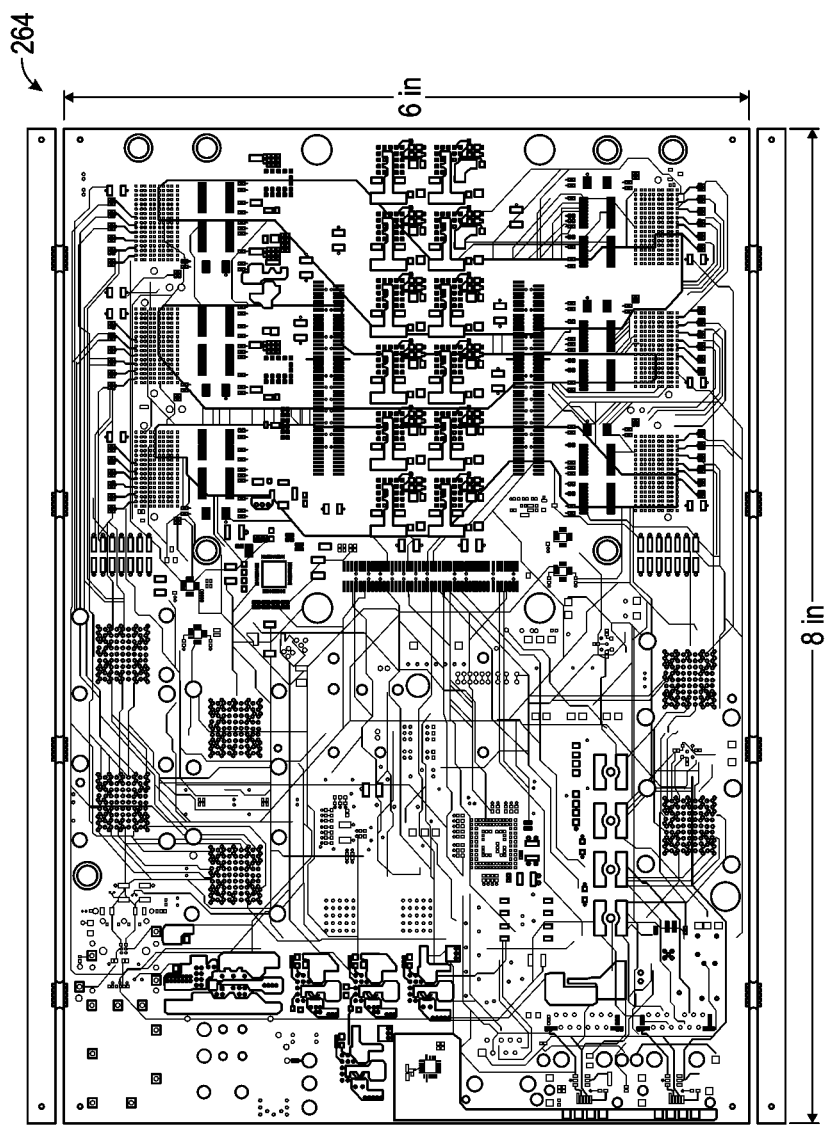
FIG. 21 illustrates a VIPIC motherboard PCB layout, in accordance with an example embodiment.
Figure 22:
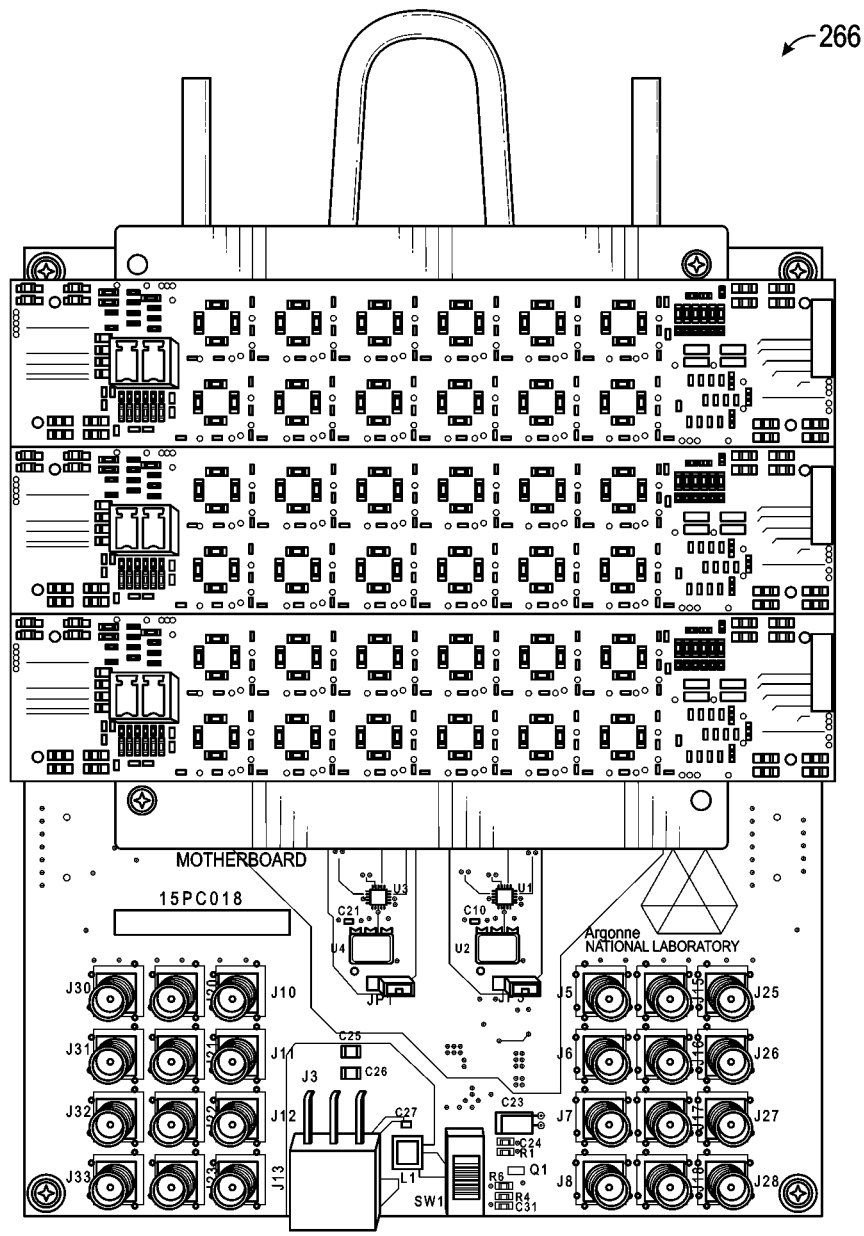
FIG. 22 illustrates an image of three VIPIC detector modules (FPGA only) on a simple VIPIC motherboard with a water cooling plate, in accordance with an example embodiment.
Figure 23:
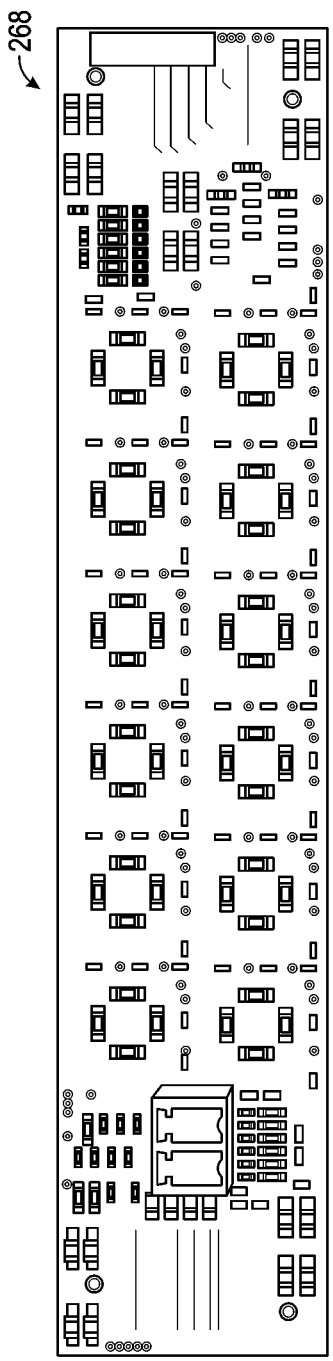
FIGS. 23-24 illustrate top and bottom of a FPGA only detector module, which can be implemented in accordance with an example embodiment (Note.
Figure 24:
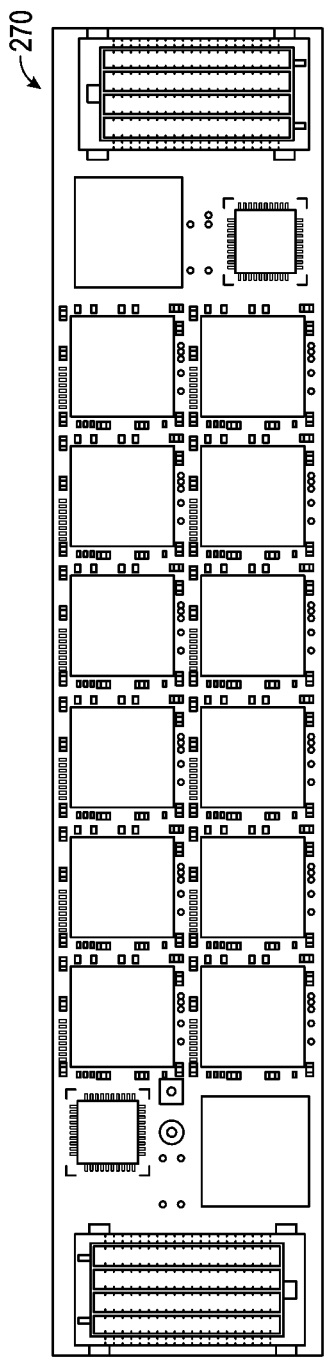
Figure 25:
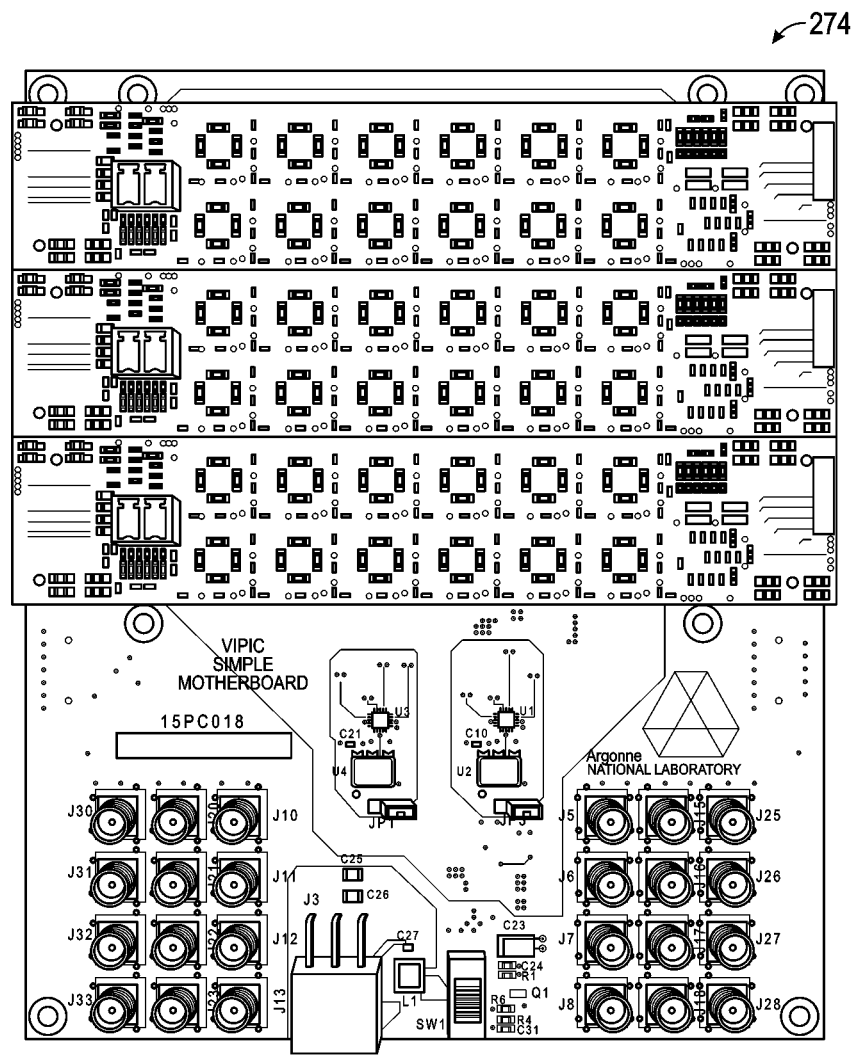
FIG. 25 illustrates an image of three VIPIC detector modules (FPGA only) on a simple VIPIC motherboard before mounting the cooling system, in accordance with an example embodiment.
Figure 26:
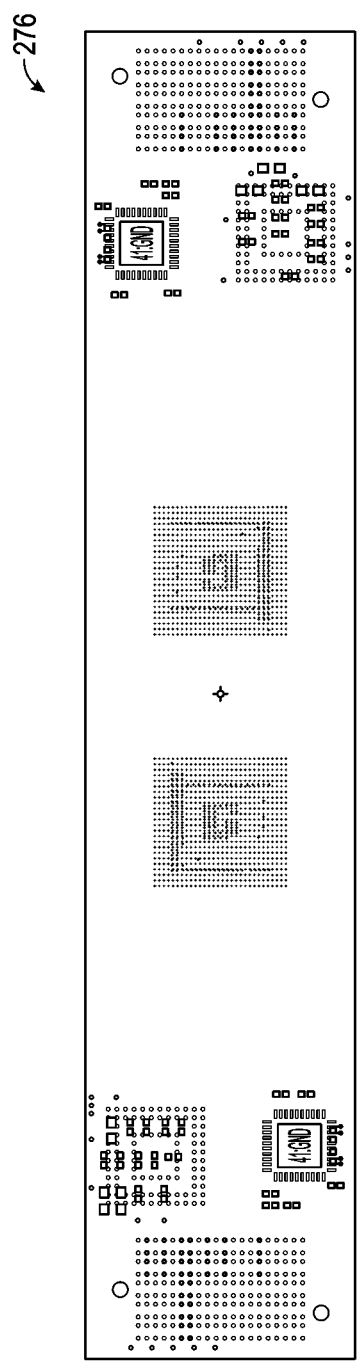
FIG. 26 illustrates a VIPIC detector module with connection pattern to two 3D ASICs, in accordance with an example embodiment.
Figure 27:
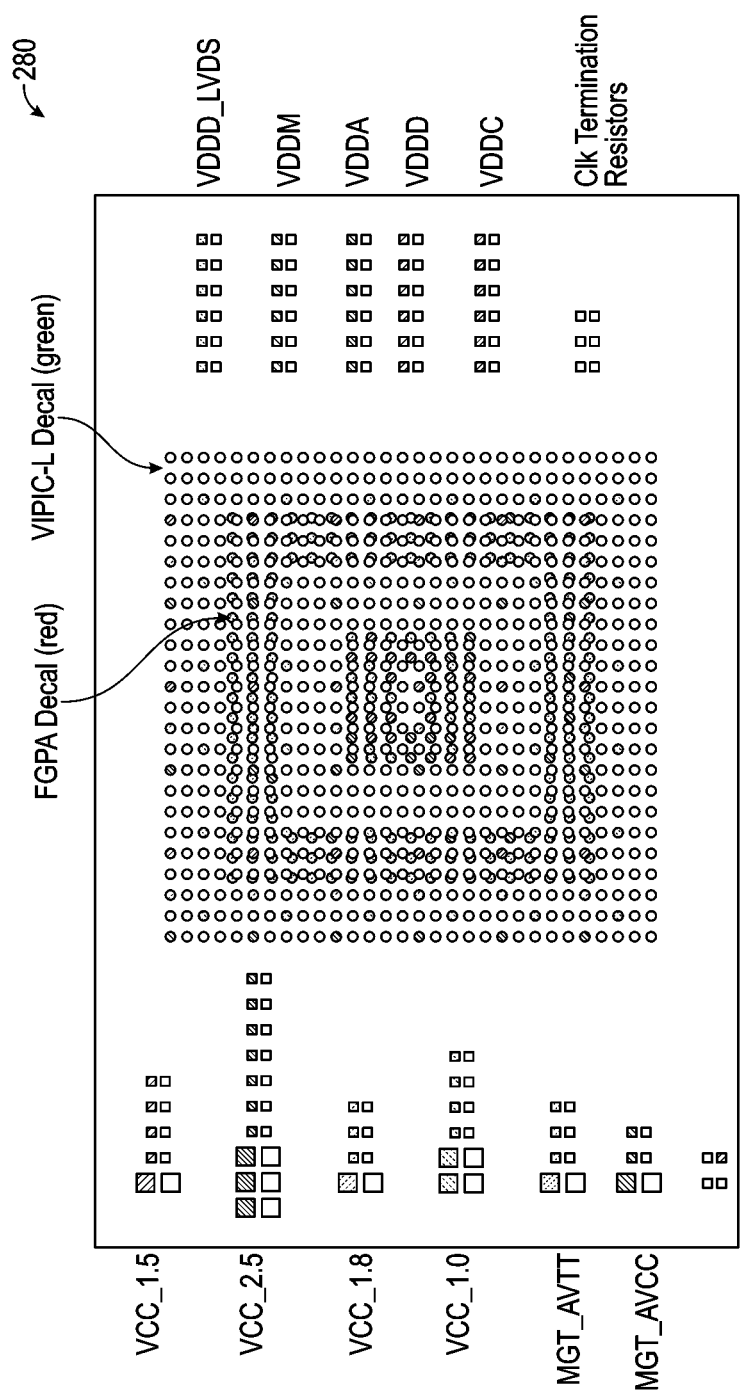
FIG. 27 illustrates a ball grid array pattern for an FPGA and an ASIC along with all the power supplies required for both, while demonstrating the complexity required for routing and the lack of space for mounting additional components, in accordance with an example embodiment.

The respective top and bottom image views 260 and 262 of a partially assembled motherboard are depicted in FIGS. 19 and 20, while an image 264 of a detailed layout of one of its layers is shown in FIG. 21. FIG. 22 illustrates an image 266 of three VIPIC detector modules (FPGA only) on a simple VIPIC motherboard with a water cooling plate, in accordance with an example embodiment. FIGS. 23-24 illustrate respective top and bottom views 268 and 270 of the image of an FPGA only detector module, which can be implemented in accordance with an example embodiment. Note that FIG. 23 depicts thermal resistors instead of VIPIC ASIC's for thermal dissipation studies). FIG. 25 illustrates an image 274 of three VIPIC detector modules (FPGA only) on a simple VIPIC motherboard before mounting the cooling system, in accordance with an example embodiment. FIG. 26 illustrates the layout 276 of a VIPIC detector module with connection pattern to two 3D ASICs, in accordance with an example embodiment.

Note that PicoZED module is a commercial board that simplifies the software and hardware development needed to communicate and control the detector head. The PicoZED module offers a Xilinx Zynq FPGA running Linux on its dual ARM processors. Thus, the PicoZED module allows for development in a Linux environment similar to that of, for example, a Linux computer. In addition to the ARM processors, the Xilinx Zynq has a reprogrammable FPGA section, allowing for the development of custom logic to perform task that cannot be handled by the Linux software.

Figure 18:
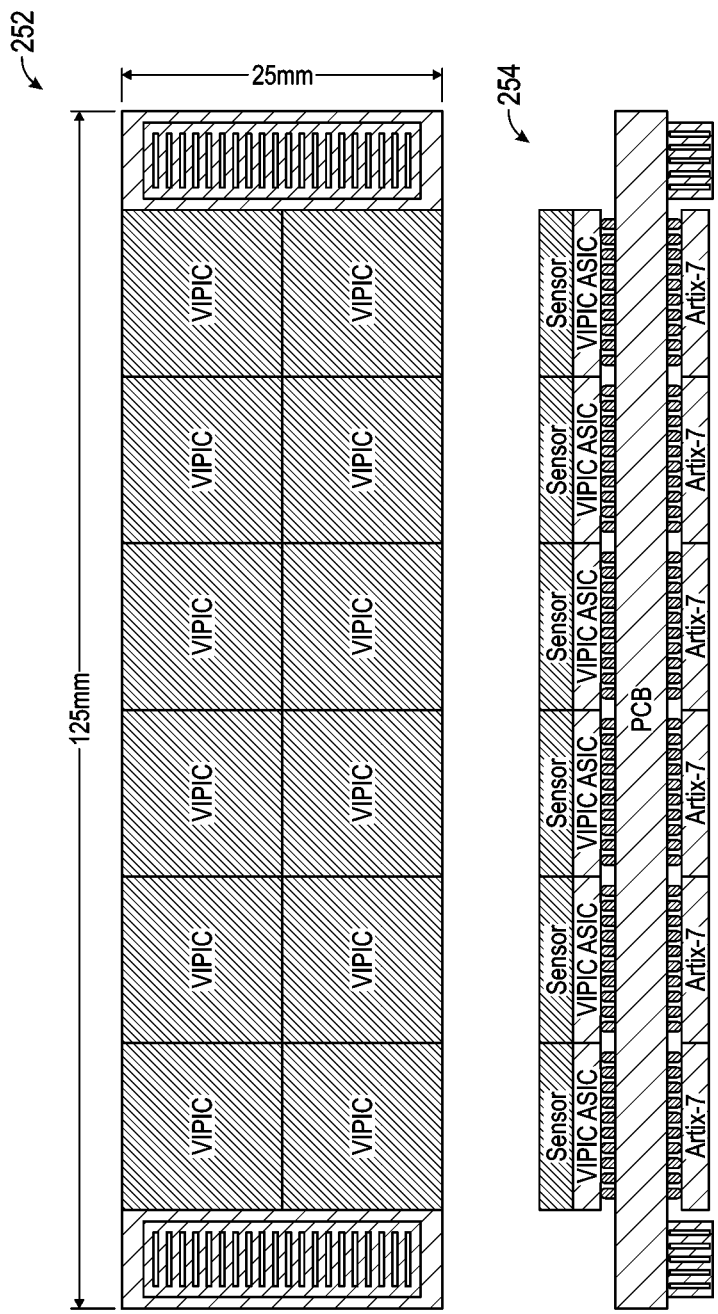
FIG. 18 illustrates top and side views of a detector module, in accordance with an example embodiment.

FIG. 18 illustrates the top view 252 and a side view 254 assembly of a detector module on an electrical substrate (PCB or ceramic board such as LTCC). In an example embodiment, a detector module such as shown in FIG. 18 can include an array of 2×6 3D integrated VPIC's connected on one side to the sensor and bump bonded on the opposite side to the PCB. Further as shown in the images depicted in FIG. 24, the opposite side of the PCB can be bonded to an array of 2×6 FPGA's. This configuration also contains connectors on the edges, which allow signal transfer from a detector module to the detector head 218 shown, for example, in FIG. 17.

The detector module has almost 12,000 solder bumps in an area of 25 mm×75 mm, which requires high density ball grid array packaging on both top and bottom of the printed circuit board as well as surface mount components in 01005 case sizes. The layout, routing and fabrication of this board will require state of the art techniques utilizing 24+ layers as well as via-in-pad, stacked laser drilled microvias and multiple lamination cycles.

With 12 ASICs on each detector module, each having hundreds of I/O, it was critical to minimize this interconnect as close to the front end as possible, therefore the design matches each ASIC with its own FPGA. The FPGA then consolidates all the complexities of the ASIC interconnect into a single high speed bidirectional 5 Gbps link for communication with the data acquisition system.

The Detector Module has 12 Artix FPGAs and 12 VIPIC ASICs. It is designed so that there is one Artix FPGA for each VIPIC ASIC. The Artix FPGA and VIPIC ASIC are placed on opposite sides of a PCB board making it necessary for the PCB to use buried vias in order to route the traces between the BGA (ball grid array) parts. Each Artix FPGA collects the data from its associated VIPIC ASIC over its 36 LVDS outputs from. Inside the Artix FPGA, all of this data is then concentrated into a single multi-gigabit transmitter. This transmitter can be routed through the VIPIC detector head to a miniPOD transmit fiber. In this manner, the data from each VIPIC ASIC can be concentrated into a single fiber output.

The cooling system can be composed of a chiller and a heat exchanger. The heat exchange is within the detector head and located between the VIPIC mother board and the three Detector Modules The Power Supply can provide power to the detector head. The power goes into the VIPIC mother board which generates all of the various voltages need by the PicoZED board and the detector module. The voltages needed by the detector module are for the Artix FPGAs and the VIPIC ASIC.

The user interface computer can be implemented as a computer on the same subnet as the detector head. The interface computer runs software that allows a user to control and configure the detector head and data acquisition system. The data acquisition system receives all of the data from the detector head and is responsible for storing and/or processes the data.

Based on the foregoing, it can be appreciated that a number of example embodiments, preferred and alternative, are disclosed herein. For example, in one embodiment, a detecting apparatus can be implemented which is composed of a multi-tier 3D integrated ASIC comprising at least one analog tier and at least one digital tier; a sensor bonded to the multi-tier 3D integrated ASIC; an electrical substrate; a plurality of FPGAs or custom data management ASICs; a thermal management system; a power distribution system; and a plurality of connectors to transfer data to a data acquisition system configured for radiation spectroscopy or imaging with zero suppressed or full frame readout.

In some example embodiments, the aforementioned electrical substrate can be a ceramic or a material based readout board. In another example embodiment, a dead-time-less operation can be provided, which continuously processes signals within user defined time frames. In some example embodiments, a segmented sensor can be implemented with a plurality of sensor pixels and a matching segmented analog tier with a plurality of analog pixels. Each analog pixel among the plurality of analog pixels can include one or more charge sensitive amplifiers with sensor leakage current compensation, and can also include, for example, a shaping filter, one or more comparators, and at least one trimming digital to analog converter (DAC). The at least one digital tier can be configured with a digital functionality for processing signals from the plurality of analog pixels of the at least one analog tier and transfers data off multi-tier 3D integrated ASIC.

In some example embodiments, the multi-tier 3D integrated ASIC can be die-to-wafer bonded to a sensor layer on one side and to the ceramic or a material based readout board on the other side to configure an assembly comprising a dead-zone-less detector module.

The dead-zone-less detector module can include a plurality of additional electrical components include at least one DAC that biases the multi-tier 3D integrated ASIC, and at least one decoupling capacitor, and which performs a plurality of functions including power distribution, control and clocks from FPGA to ASICs and data transfer from ASICs to FPGA. The dead-zone-less detector module can also be configured with a plurality of connectors that receive a plurality of signals including power, biases and clocks, and which transmits high speed, multiplexed and concentrated data to a detector head.

In some example embodiments, the aforementioned detector head can be configured to contain a plurality of detector modules, and a thermal management system for power dissipation placed in proximity to the plurality of detector modules. The detector head can transfer a large volume of high-speed data to a Data Acquisition (DAQ) system for further processing or storage of the data. The detector head can also include additional circuitry and components that allow the detector head to function as a data concentrator, receiving data from a plurality of ASICs processing the data and sending the data to the DAQ for further processing.

In an example embodiment, the multi-tier 3D integrated ASIC includes the at least one analog and the at least one digital tier, which are precisely diced, and then die-to-wafer bonded to a sensor layer on one side such that a resulting assembly constitutes either a dead-zone-less detector module or allows for a minimum gaps between ASICs.

In another example embodiment, a method of configuring a detecting apparatus can be implemented, which includes processing or fabrication steps such as, for example, providing an electrical substrate; providing a multi-tier 3D integrated ASIC comprising at least one analog tier and digital tier; bonding a sensor to the multi-tier 3D integrated ASIC; providing a plurality of FPGAs or custom data management ASICs: configuring a thermal management system; providing a power distribution system; and configuring a plurality of connectors to transfer data to a data acquisition system configured for radiation spectroscopy or imaging with zero suppressed or full frame readout.

In another example embodiment, processing or fabrication steps can be implemented, such as, for example: configuring the at least one analog tier and the at least one digital tier utilizing a CMOS process, and subsequently a face-to-face bonded operation; thinning the at least one digital tier to a few micrometers of Si; adding TSV in the at least one digital tier TSV and/or exposing previously buried TSV's; adding back metal pads to render connections to TSV's; adding a handle wafer covering up pads; flipping over an assembly and thinning the at least one analog tier to a few micrometers of Si; adding TSV in the at least one analog tier TSV or exposing previously buried TSV's; adding temporary metal pads to a periphery where test connections were pre-routed; testing a subset of analog and digital functionalities to verify a design as well as a successful 3D assembly to identify Known Good Dies (KGD); removing temporary pads; preparing a surface for back-to-face bonding of a back face of an analog and front face of a sensor; precisely dicing a 3D assembled wafer without destroying chip edges; utilizing KGD to die-to-wafer bonding to sensor with minimum gaps; removing handle material from a digital side to expose buried pads; flipping and bump-bonding to a ceramic or a material based board; flipping and bonding FPGAs on an opposite side; populating all other circuit components to create a detector module; and altering the order of bonding ASICs, FPGAs and other circuit to accommodate bonding requirements.

It can be appreciated that the example embodiments discussed and illustrated herein serve only as examples to illustrate several ways of implementation of the present disclosure. Such example embodiments should not be construed as to limit the spirit and scope of the present disclosure. It should be noted that those skilled in the art may still make various modifications or variations without departing from the spirit and scope of the disclosed example embodiments. Such modifications and variations shall fall within the protection scope of the embodiments, as defined in attached claims.

The invention claimed is:

1. A detecting apparatus head, comprising:
   a mother board electronically and mechanically connected to at least one dead-zone-less detector module having a substrate;
   at least one multi-tier 3D integrated ASIC (Application-Specific Integrated Circuit) comprising at least one analog tier and at least one digital tier connected to at least one segmented sensor, wherein at least one tier of said at least one multi-tier 3D integrated ASIC is bonded to said at least one segmented sensor and at least one tier of said at least one multi-tier 3D integrated ASIC is bonded to said substrate of said at least one dead-zone-less detector module;
   at least one data processing, computation, and transmission circuit, wherein said at least one data processing, computation, and transmission circuit is mounted onto a side of said at least one dead-zone-less detector module opposite said at least one multi-tier 3D integrated ASIC;
   a thermal management system comprising a cooling system that includes a chiller and a heat exchanger, wherein said heat exchanger is located within said detecting apparatus head and between said motherboard and said at least one dead-zone-less detector module.

2. The detecting apparatus head of claim 1 further comprising a power distribution system that includes at least one power supply that supplies power from said motherboard to said at least one dead-zone-less detector module.

3. The detecting apparatus head of claim 1 comprising a dead-time-less operation that continuously processes signals within user defined time frames.

4. The detecting apparatus head of claim 1 further comprising said at least one segmented sensor with a plurality of sensor pixels and a matching segmented analog tier with a plurality of analog pixels.

5. The detecting apparatus head of claim 4 wherein each analog pixel among said plurality of analog pixels includes at least a charge sensitive amplifier with sensor leakage current compensation, a shaping filter, at least one comparator, and at least one trimming digital to analog converter (DAC).

6. The detecting apparatus head of claim 4 wherein said at least one digital tier comprises a digital functionality for processing signals from said plurality of analog pixels of said at least one analog tier and transfers data off said at least one multi-tier 3D integrated ASIC.

7. The detecting apparatus lead of claim 2 wherein said at least one multi-tier 3D integrated ASIC is die-to-wafer bonded to a sensor layer of said at least one segmented sensor to configure an assembly comprising said at least one dead-zone-less detector module.

8. The detecting apparatus head of claim 7 wherein said at least one dead-zone-less detector module further comprises a plurality of additional electrical components which performs a plurality of functions including power distribution, distributes control and docks from said at least one data processing, computation, and transmission circuit and transfers data from said at least one multi-tier 3D integrated circuit to said at least one data processing, computation, and transmission circuit.

9. The detecting apparatus head of claim 7 wherein said at least one dead-zone-less detector module receives a plurality of signals including power, biases and clocks, and which transmits high speed, multiplexed and concentrated data to said motherboard of said detecting apparatus head.

10. The detecting apparatus head of claim 1 further comprising wherein said at least one dead-zone-less detector module, and said thermal management system for power dissipation placed in proximity to said at least one dead-zone-less detector module making direct contact to said at least one dead-zone-less detector module for heat exchange.

11. The detecting apparatus head of claim 9 wherein said detecting apparatus head transfers a large volume of high-speed data to a Data Acquisition (DAQ) system external to said detecting apparatus head for further processing or storage of said data.

12. The detecting apparatus head of claim 7 wherein said at least one dead-zone-less detector module includes additional circuitry and components that allow said at least one dead-zone-less detector module to function as a data concentrator, receiving data from said at least one multi-tier 3D integrated ASIC, processing said data and moving said data to said motherboard and then to said DAQ for further processing.

13. The detecting apparatus head of claim 1 wherein said at least one multi-tier 3D integrated ASIC comprises at least one analog tier and at least one digital tier, which are diced in a manner that a size of said at least one multi-tier 3D integrated ASIC is known after dicing with a precision better than a size of a gap planned between said at least one multi-tier 3D integrated ASIC to be placed one next to another on said at least one segmented sensor, and then die-to-wafer bonded to a sensor layer on one side such that a resulting assembly constitutes either said at least one dead-zone-less detector module or allows for a minimum gaps between ASICs.

14. The detecting apparatus head of claim 1 wherein said at least one multi-tier 3D integrated ASIC comprises at least one analog tier and at least one digital tier, which are diced in a manner wherein said at least one multi-tier 3D integrated ASIC possesses a same dimension as another said at least one multi-tier 3D integrated ASIC and does not include a peripheral material that results in uneven sizes of various dies.

* * * * *